US012661524B2

(12) United States Patent
Nazarian et al.

(10) Patent No.: US 12,661,524 B2
(45) Date of Patent: Jun. 23, 2026

(54) MASK WITH VIBRATION AND LIGHT THERAPY

(71) Applicant: Therabody, Inc., Los Angeles, CA (US)

(72) Inventors: Benjamin Nazarian, Los Angeles, CA (US); Jaime Sanchez Solana, Los Angeles, CA (US); Eduardo Merino, Los Angeles, CA (US); Thomas Cisneros, Los Angeles, CA (US); Mandar Deshmukh, Los Angeles, CA (US)

(73) Assignee: Therabody, Inc., Los Angeles, CA (US)

( * ) Notice: Subject to any disclaimer, the term of this patent is extended or adjusted under 35 U.S.C. 154(b) by 0 days.

(21) Appl. No.: 18/165,864

(22) Filed: Feb. 7, 2023

(65) Prior Publication Data

US 2024/0261586 A1 Aug. 8, 2024

Related U.S. Application Data

(63) Continuation-in-part of application No. 17/929,571, filed on Sep. 2, 2022, now Pat. No. 12,520,929.

(Continued)

(51) Int. Cl.
*A61N 5/00* (2006.01)
*A61N 5/06* (2006.01)

(52) U.S. Cl.
CPC .... *A61N 5/0616* (2013.01); *A61N 2005/0642* (2013.01); *A61N 2005/0647* (2013.01);
(Continued)

(58) Field of Classification Search
CPC .......... A61N 5/0616; A61N 2005/0642; A61N 2005/0647; A61N 2005/0651; A61N 2005/0659; A61N 2005/0663
See application file for complete search history.

(56) References Cited

U.S. PATENT DOCUMENTS

| | | | |
|---|---|---|---|
| 1,545,027 A | 7/1925 | Ashlock | |
| D143,678 S | 1/1946 | Snyder et al. | |
| (Continued) | | | |

FOREIGN PATENT DOCUMENTS

| | | | |
|---|---|---|---|
| CN | 201239336 Y | 5/2009 | |
| CN | 301664182 S | 9/2011 | |
| (Continued) | | | |

OTHER PUBLICATIONS

International Search Report and Written Opinion of the International Searching Authority directed to related International Patent Application No. PCT/US2019/039444, mailed Sep. 9, 2019, with attached English-language translation; 10 pages.
(Continued)

*Primary Examiner* — Sana Sahand
(74) *Attorney, Agent, or Firm* — Sterne, Kessler, Goldstein & Fox P.L.L.C.

(57) ABSTRACT

Described herein are components, systems, and methods for a face mask and mask system that includes vibration and light therapy. A mask apparatus includes a mask portion, an eye portion coupled to the inner layer of the mask portion, one or more openings extending through the mask portion and the eye portion, and a strap coupled to the mask portion. The mask portion includes an outer layer, one or more middle layers comprising a plurality of light emitting diodes (LEDs) and one or more printed circuit board (PCB) members, and an inner layer. The eye portion includes a silicone layer configured to cover an area around a user's eyes and a first plurality of vibration motors encapsulated in the silicone layer.

21 Claims, 25 Drawing Sheets

Related U.S. Application Data

(60) Provisional application No. 63/240,042, filed on Sep. 2, 2021.

(52) U.S. Cl.
CPC ................ *A61N 2005/0651* (2013.01); *A61N 2005/0659* (2013.01); *A61N 2005/0663* (2013.01)

(56) References Cited

U.S. PATENT DOCUMENTS

| | | | |
|---|---|---|---|
| 2,987,334 | A | 6/1961 | Wendling |
| 3,015,105 | A | 1/1962 | Rogowski |
| 3,517,392 | A | 6/1970 | Hodge et al. |
| 3,705,579 | A | 12/1972 | Morini et al. |
| D229,375 | S | 11/1973 | Andre |
| D230,522 | S | 2/1974 | Rothman |
| 4,046,142 | A | 9/1977 | Whitney |
| 4,996,981 | A | 3/1991 | Elenewski et al. |
| 5,103,809 | A | 4/1992 | DeLuca et al. |
| D423,726 | S | 4/2000 | Backus |
| D439,984 | S | 4/2001 | Thach |
| 6,524,329 | B1 | 2/2003 | Benedict |
| 6,823,762 | B2 | 11/2004 | Hu |
| 6,974,224 | B2 | 12/2005 | Thomas-Benedict |
| 7,431,706 | B2 | 10/2008 | Louis |
| 7,927,259 | B1 | 4/2011 | Rix |
| 7,927,294 | B2 | 4/2011 | Kamimura et al. |
| D659,644 | S | 5/2012 | Gretz |
| 8,777,881 | B2 | 7/2014 | Tsai |
| D745,694 | S | 12/2015 | Tapper et al. |
| D745,695 | S | 12/2015 | Tapper et al. |
| D756,180 | S | 5/2016 | Chen |
| 9,889,066 | B2 | 2/2018 | Danby et al. |
| D817,732 | S | 5/2018 | Rettler |
| D836,835 | S | 12/2018 | Hazem |
| D837,395 | S | 1/2019 | Gan |
| D870,905 | S | 12/2019 | Xiong |
| D881,380 | S | 4/2020 | Cartwright |
| D884,964 | S | 5/2020 | Wang |
| D891,629 | S | 7/2020 | Vetu et al. |
| D894,412 | S | 8/2020 | Kim |
| D901,029 | S | 11/2020 | Song |
| D909,674 | S | 2/2021 | Xiong et al. |
| D957,661 | S | 7/2022 | Kwon et al. |
| D973,895 | S | 12/2022 | Yi |
| D975,090 | S | 1/2023 | Deshmukh et al. |
| 2004/0162549 | A1 | 8/2004 | Altschuler |
| 2005/0070977 | A1 | 3/2005 | Molina |
| 2006/0217690 | A1 | 9/2006 | Bastin et al. |
| 2011/0251532 | A1 | 10/2011 | Yang |
| 2013/0196284 | A1* | 8/2013 | Brawn .................... A61C 7/00 |
| | | | 433/24 |
| 2014/0222026 | A1 | 8/2014 | Tenenbaum et al. |
| 2014/0350643 | A1 | 11/2014 | Pepitone et al. |
| 2015/0190607 | A1 | 7/2015 | Sugio et al. |
| 2016/0367425 | A1 | 12/2016 | Wersland |
| 2017/0042754 | A1 | 2/2017 | Fowers et al. |
| 2017/0304145 | A1 | 10/2017 | Pepe |
| 2018/0141188 | A1 | 5/2018 | Lai |
| 2021/0330539 | A1 | 10/2021 | Faussett |
| 2021/0370090 | A1* | 12/2021 | Lay ........................ A61N 5/062 |
| 2022/0080221 | A1 | 3/2022 | Gross |
| 2022/0241146 | A1* | 8/2022 | Jeong .................. A61N 5/0616 |
| 2022/0257971 | A1 | 8/2022 | Kim et al. |
| 2023/0062185 | A1 | 3/2023 | Nazarian et al. |

FOREIGN PATENT DOCUMENTS

| | | | | |
|---|---|---|---|---|
| CN | 202637439 | U | 1/2013 | |
| CN | 303250924 | S | 6/2015 | |
| CN | 303250929 | S | 6/2015 | |
| CN | 303361276 | | 9/2015 | |
| CN | 106859949 | A | 6/2017 | |
| CN | 304428745 | | 12/2017 | |
| CN | 304561844 | S | 3/2018 | |
| CN | 207855923 | U | 9/2018 | |
| CN | 304883641 | | 11/2018 | |
| CN | 109528473 | A | 3/2019 | |
| CN | 305089254 | | 3/2019 | |
| CN | 305100323 | | 4/2019 | |
| CN | 305111250 | | 4/2019 | |
| CN | 305162746 | | 5/2019 | |
| CN | 305198194 | | 6/2019 | |
| CN | 209187922 | U * | 8/2019 | |
| CN | 305571116 | | 1/2020 | |
| CN | 305692322 | | 4/2020 | |
| CN | 305692323 | | 4/2020 | |
| CN | 305747614 | | 4/2020 | |
| CN | 210750922 | U * | 6/2020 | |
| CN | 210933465 | U * | 7/2020 | |
| CN | 305984378 | | 8/2020 | |
| CN | 306006367 | | 8/2020 | |
| CN | 306048936 | | 9/2020 | |
| CN | 306554308 | | 5/2021 | |
| CN | 306572521 | | 5/2021 | |
| CN | 306813805 | | 9/2021 | |
| CN | 306828018 | | 9/2021 | |
| CN | 307260712 | | 4/2022 | |
| CN | 307493334 | | 8/2022 | |
| CN | 307602529 | | 10/2022 | |
| EP | 0038628530001 | | 9/2017 | |
| EP | 0057976360001 | | 11/2018 | |
| GB | 90038628530001 | | 4/2017 | |
| GB | 90057976360001 | | 10/2018 | |
| HK | 16024590001 | | 7/2017 | |
| JP | S5428491 | A | 3/1979 | |
| JP | H0447440 | U | 4/1992 | |
| JP | 2000189525 | A | 7/2000 | |
| JP | 2011502369 | A | 1/2011 | |
| JP | 5129032 | B2 | 1/2013 | |
| JP | 2014511240 | A | 5/2014 | |
| JP | 1534873 | S | 10/2015 | |
| JP | 1645293 | S | 11/2019 | |
| JP | 1661460 | S | 6/2020 | |
| KR | 200292048 | Y1 * | 10/2002 | |
| KR | 101122679 | B1 * | 3/2012 | .......... A45D 44/002 |
| KR | 101162978 | B1 | 7/2012 | |
| KR | 3007103830000 | | 9/2013 | |
| KR | 3007574890000 | | 8/2014 | |
| KR | 20160095878 | A * | 2/2015 | |
| KR | 101637343 | B1 * | 7/2016 | |
| KR | 20170108550 | A | 9/2017 | |
| KR | 102097298 | B1 * | 7/2019 | .......... A45D 44/002 |
| KR | 3010132580000 | | 7/2019 | |
| KR | 3010132590000 | | 7/2019 | |
| KR | 20190121715 | A * | 10/2019 | |
| KR | 20200112260 | A | 10/2020 | |
| KR | 20220042012 | A | 4/2022 | |
| KR | 3011616400000 | | 6/2022 | |
| TW | I359657 | B | 3/2012 | |
| TW | 2054440001 | | 6/2020 | |
| TW | 2054460001 | | 6/2020 | |
| WO | WO-2009004412 | A1 * | 1/2009 | .......... A61N 5/0614 |
| WO | WO-2020/263258 | A1 | 12/2020 | |
| WO | WO-2020251310 | A1 * | 12/2020 | ............... A61F 7/00 |

OTHER PUBLICATIONS

Anthony Katz, "The Raptor: Helps Patients and Saves Your Most Valuable Tool . . . Your Hands," DC Aligned: MeyerDC, Dec. 9, 2015, available at: http://news.meyerdc.com/community/vendor-spotlight/the-raptor-helps-patients-saves-your-most-valuable-tool-your-hands/ (last visited Feb. 15, 2023); 5 pages.

Defendant's Initial Invalidity Contentions, *Therabody, Inc.* v. *Tzumi Electronics LLC et al.*, Case No. SDNY-1-21-cv-07803 (PGG)(RWL), dated Aug. 17, 2022; 16 pages.

Description of Therabody GI Device, available at: https://www.therabody.com/US/en-us/faq/thearagun-devices/faq-devices-1.html?fdid=faq&csortb1=sortOrder&csortd1=1 (last visited Feb. 15, 2023).

Holly Riddle, "Theragun vs. Hyperice vs, Hydragun: Massage Gun Showdown [Buyer's Guide]," ChatterSource: Health & Wellness,

(56) References Cited

OTHER PUBLICATIONS

Mar. 9, 2021, available at: https://www.chattersource.com/article/massage-gun/ (last visited Feb. 17, 2023); 14 pages.
Visual Description of Hyper Ice, Inc. Raptor Device, "Osteopatia Haidy Ortale—Raptor Massage," available at: https://www.youtube.com/watch?v=plyW8FBowVs (last visited Feb. 15, 2023); 1 page.
Visual Description of Hyper Ice, Inc. Raptor Device, "Raptor Solutions 1.3 Prone," available at: https://www.youtube.com/watch?v=6i1tRqdwPU8&t=156s (last visited Feb. 15, 2023); 1 page.
International Search Report and Written Opinion for Application No. PCT/US2023/072746, mailed on Nov. 30, 2023, 12 pages.

* cited by examiner

MASK WITH VIBRATION AND LIGHT THERAPY

CROSS-REFERENCE TO RELATED APPLICATIONS

This application is a continuation-in-part of U.S. non-provisional application Ser. No. 17/929,571 filed Sep. 2, 2022, which claims the benefit of U.S. Provisional Application No. 63/240,042, filed on Sep. 2, 2021, the disclosures of which are incorporated by reference herein in their entireties.

BACKGROUND

Field

The present disclosure relates to components, systems, and methods for a face mask and mask system that includes vibration therapy and light therapy.

Background

As people age, devices for skin and facial care are needed. Light therapy may be beneficial for treating skin for acne, stimulating collagen and elastin, minimizing redness and wrinkles, and the like. In particular, light-emitting diode (LED) therapy may be incorporated in facial treatment technology during a treatment at a spa or at a doctor's office. People may desire to access such treatments from the comfort of their home or outside of an in-office procedure. Current technologies for skincare light therapy may be limited, and devices such as at-home light therapy devices might not provide additional modalities for combining different therapies in a single device for users.

BRIEF SUMMARY

Accordingly, there may be a need for providing new methods, devices, and systems for providing LED light therapy and vibration therapy to users in a mask. The present disclosure is a mask system that combines light therapy technology of different wavelengths (e.g., red, blue, amber, and/or infrared) with low-amplitude vibration therapy. By combining both therapies, the benefits from LED light therapy (e.g., collagen increase, reduction of bacteria that creates acne, etc.) are enhanced by the increase in blood and oxygen flow created by the vibration therapy.

In some embodiments, the light therapy is delivered by an array of single-color and/or multi-color light emitting diodes (LEDs) attached to, secured within or otherwise associated with the mask (e.g., attached to the inner surface of the mask, secured between mask layers, etc.). In some embodiments, the device can have between 10-1000 LEDs, and in some embodiments includes 200-300 LEDs.

In some embodiments, the vibration therapy treatment is delivered by several small-amplitude vibrating electric motors placed throughout, attached to, secured within or otherwise associated with the mask (e.g., attached to the inner surface of the mask, secured between mask layers, etc.).

In some embodiments, the device and/or system also includes a software application downloadable to a portable electronic device that includes the ability to control the treatment and build different protocols via Bluetooth and the like.

In some embodiments, the device includes a proximity sensor that detects the distance between the device and the user's face to dim and/or turn off the LED (or other treatment protocol) and to prevent eye safety or other skin safety issues or concerns.

In an embodiment, an example mask apparatus is described. The mask apparatus includes a mask portion, an eye portion coupled to the inner layer of the mask portion, one or more openings extending through the mask portion and the eye portion, and a strap coupled to the mask portion. The mask portion includes an outer layer, one or more middle layers comprising a plurality of light emitting diodes (LEDs) and one or more printed circuit board (PCB) members, and an inner layer. The eye portion includes a silicone layer configured to cover an area around a user's eyes and a first plurality of vibration motors encapsulated in the silicone layer.

In another embodiment, an example method is described. The method includes obtaining a mask apparatus. The mask apparatus comprises a mask portion, an eye portion, one or more openings for a user's eyes, and a strap coupled to the mask portion. The mask portion comprises an outer layer, one or more middle layers comprising a plurality of light emitting diodes (LEDs) and one or more printed circuit board (PCB) members, and an inner layer. The eye portion comprises a silicone layer configured to cover an area around a user's eyes and a first plurality of vibration motors encapsulated in the silicone layer. The one or more openings extend through the mask portion and the eye portion. The method further includes positioning the mask apparatus over a user's face, and providing, to the user's face, at least one of vibration therapy through one or more vibration motors of the first plurality of vibration motors and light therapy through one or more LEDs of the plurality of LEDs to the user's face.

Further features and advantages, as well as the structure and operation of various embodiments, are described in detail below with reference to the accompanying drawings. It is noted that the specific embodiments described herein are not intended to be limiting. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form a part of the specification, illustrate embodiments of the present disclosure and, together with the description, further serve to explain the principles of the disclosure and to enable a person skilled in the pertinent art to make and use the disclosure.

Figure 1:
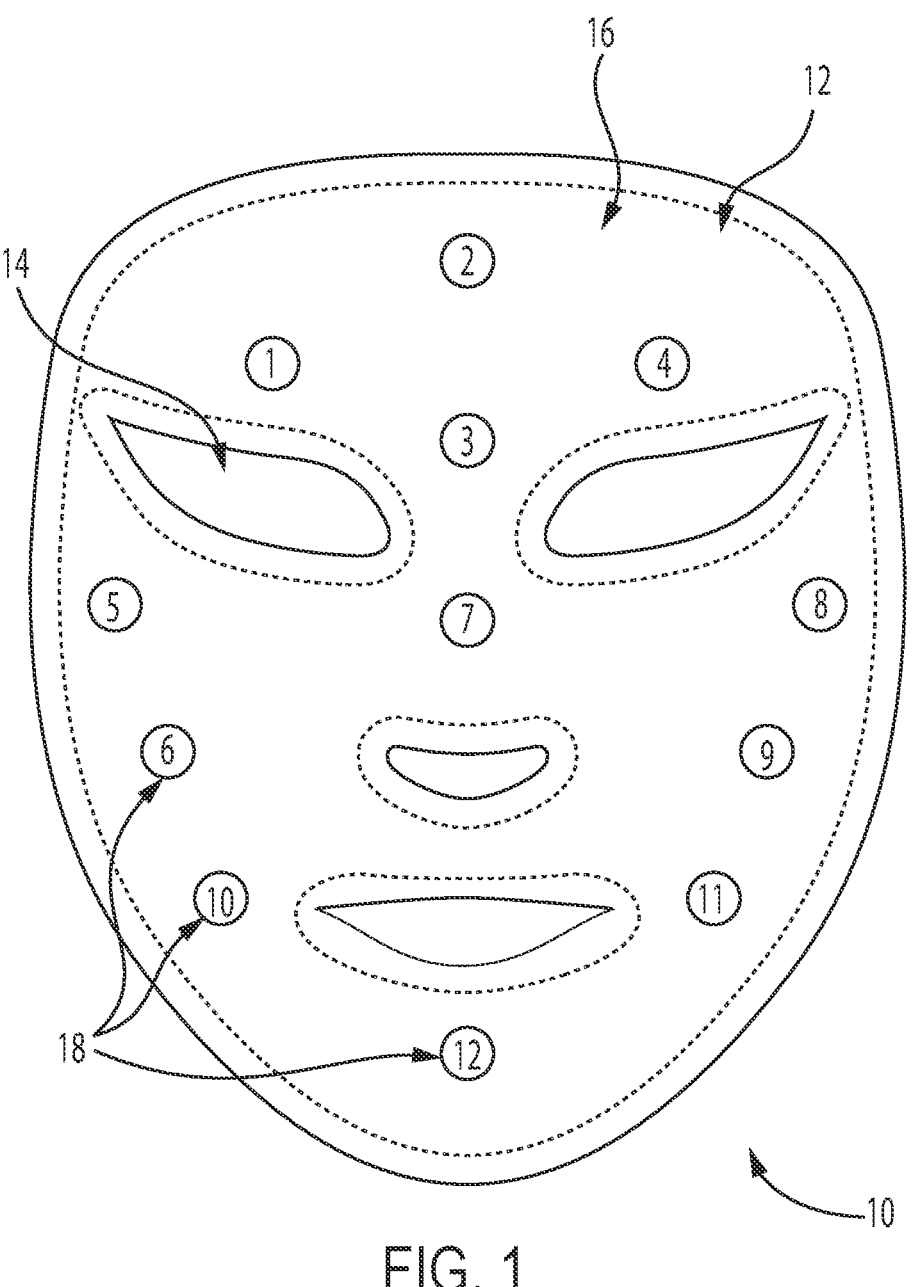
FIG. 1 illustrates an example diagram of a face mask and system that includes vibration therapy and light therapy, according to embodiments of the present disclosure.

Embodiments of the present disclosure will be described with reference to the accompanying drawings.

DETAILED DESCRIPTION

The following Detailed Description refers to accompanying drawings to illustrate exemplary embodiments consistent with the disclosure. References in the Detailed Description to "one exemplary embodiment," "an exemplary embodiment," "an example exemplary embodiment," etc., indicate that the exemplary embodiment described may include a particular feature, structure, or characteristic, but every exemplary embodiment might not necessarily include the particular feature, structure, or characteristic. Moreover, such phrases are not necessarily referring to the same exemplary embodiment. Further, when a particular feature, structure, or characteristic is described in connection with an exemplary embodiment, it is within the knowledge of those skilled in the relevant art(s) to affect such feature, structure, or characteristic in connection with other exemplary embodiments whether or not explicitly described.

The exemplary embodiments described herein are provided for illustrative purposes, and are not limiting. Other exemplary embodiments are possible, and modifications may be made to the exemplary embodiments within the spirit and scope of the disclosure. Therefore, the Detailed Description is not meant to limit the invention. Rather, the scope of the invention is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc. Further, any of the implementation variations may be carried out by a general purpose computer, as described below.

For purposes of this discussion, any reference to the term "module" shall be understood to include at least one of software, firmware, or hardware (such as one or more of a circuit, microchip, and device, or any combination thereof), and any combination thereof. In addition, it will be understood that each module may include one, or more than one, component within an actual device, and each component that forms a part of the described module may function either cooperatively or independently of any other component forming a part of the module. Conversely, multiple modules described herein may represent a single component within an actual device. Further, components within a module may be in a single device or distributed among multiple devices in a wired or wireless manner.

The following Detailed Description of the exemplary embodiments will so fully reveal the general nature of the invention that others can, by applying knowledge of those skilled in relevant art(s), readily modify and/or adapt for various applications such exemplary embodiments, without undue experimentation, without departing from the spirit and scope of the disclosure. Therefore, such adaptations and modifications are intended to be within the meaning and plurality of equivalents of the exemplary embodiments based upon the teaching and guidance presented herein. It is to be understood that the phraseology or terminology herein is for the purpose of description and not of limitation, such that the terminology or phraseology of the present specification is to be interpreted by those skilled in relevant art(s) in light of the teachings herein.

It will be appreciated that terms such as "front," "back," "top," "bottom," "side," "short," "long," "up," "down," "aft," "forward," "inboard," "outboard" and "below" used herein are merely for ease of description and refer to the orientation of the components as shown in the figures. It should be understood that any orientation of the components described herein is within the scope of the present disclosure.

Figure 2:
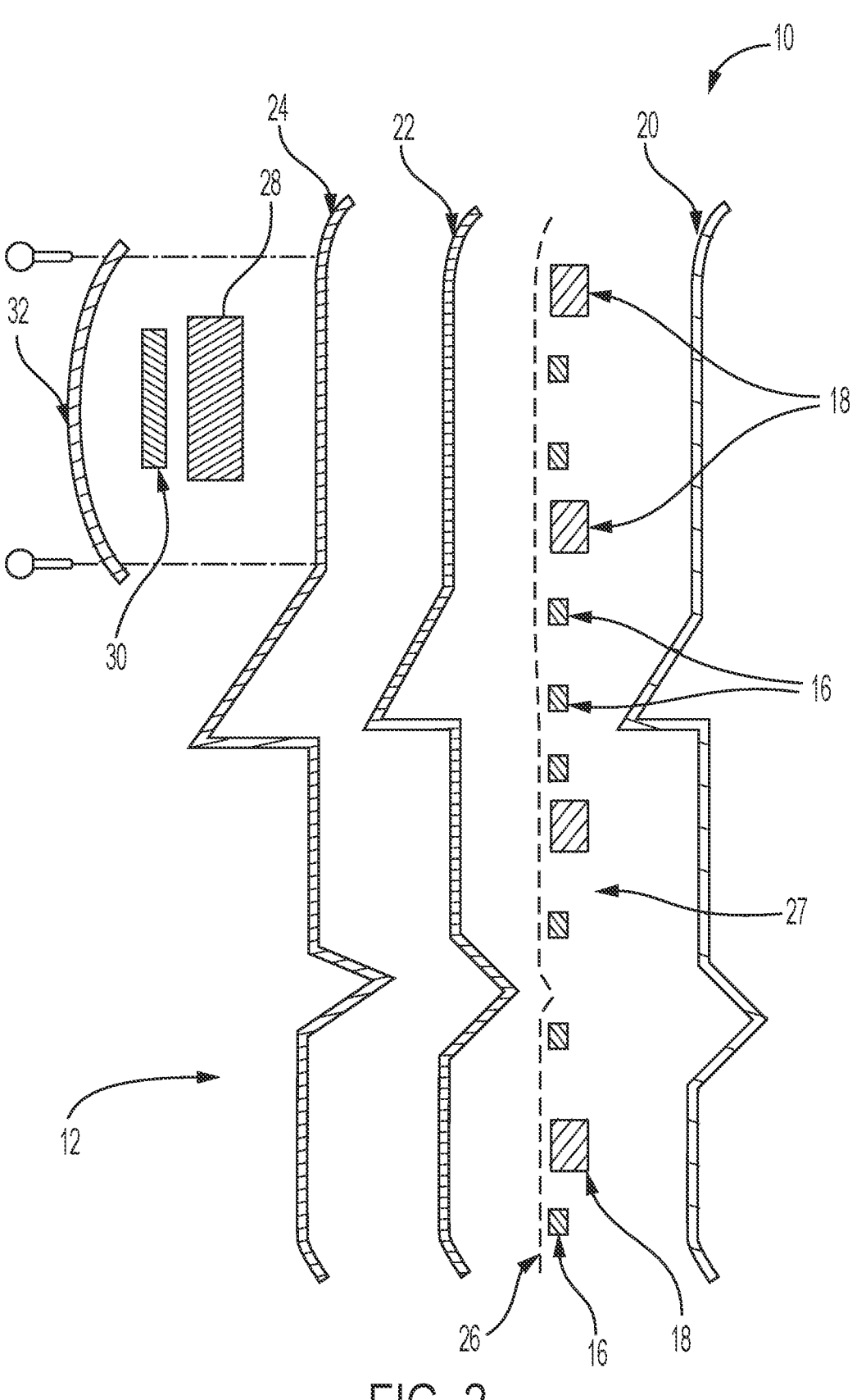
FIG. 2 illustrates a section view of a face mask, according to embodiments of the present disclosure.
Figure 3:
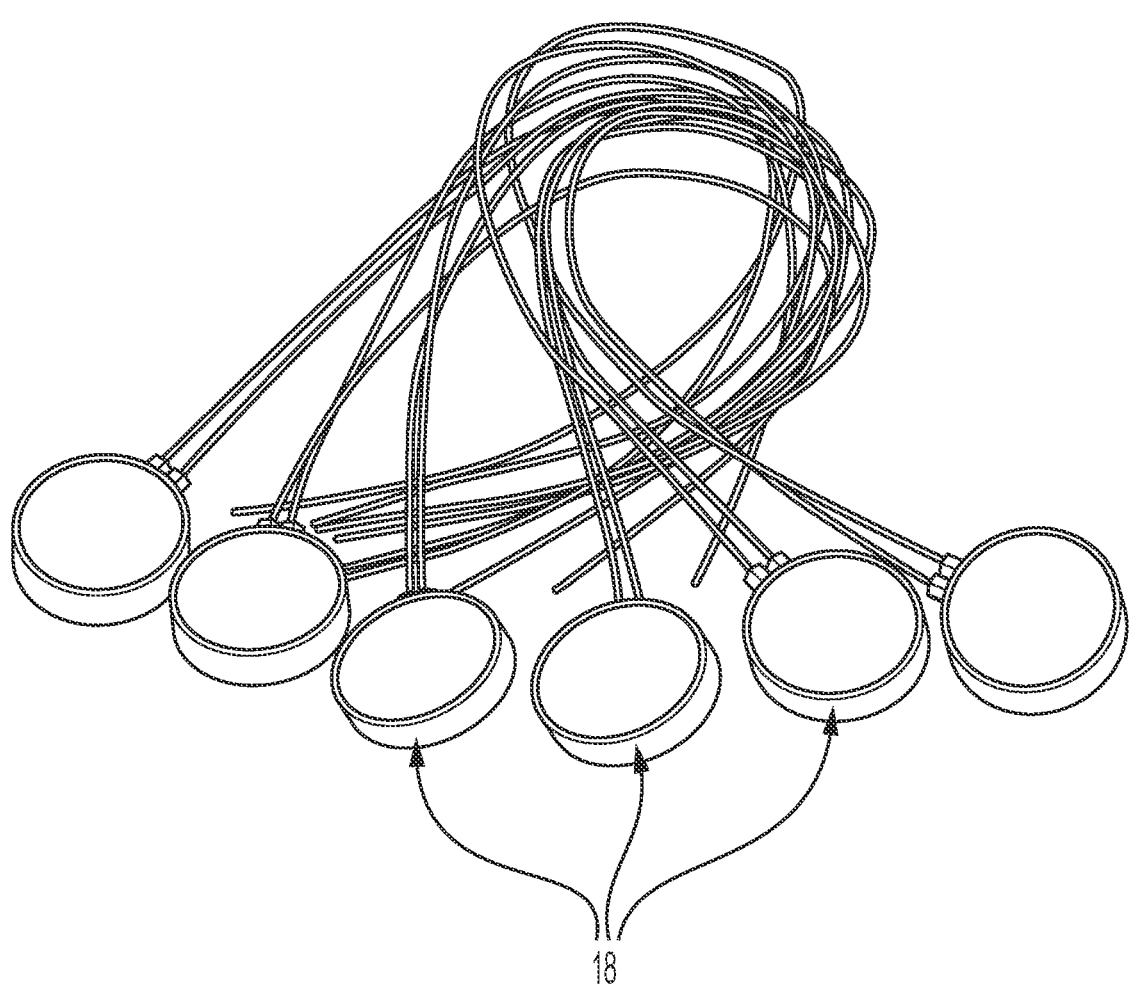
FIG. 3 illustrates exemplary vibration devices for a face mask, according to embodiments of the present disclosure.

Described herein and shown in FIGS. 1-3 is a face mask and system that includes vibration therapy and light therapy (e.g., LED, or any type of light). Examples of LED skin therapy are described in U.S. Pat. Nos. 6,524,329 and 6,974,224, the entireties of which are incorporated by reference herein.

FIGS. 1-2 illustrates a mask system 10 that combines light therapy technology of different wavelengths (e.g., red, blue, amber, and/or infrared) with low-amplitude vibration therapy. In some embodiments, the mask system 10 (and the mask portion 12 thereof) at least partially covers and targets the face and neck of the user (or one or the other thereof) and can be secured to the user's head and body to remain static during treatment.

In some embodiments, as shown in FIG. 1, the mask portion 12 is shaped to fit over a wearer's face and can include eye, nostril/nose, mouth and/or ear openings 14. In some embodiments, the mask portion 12 includes a plurality of LEDs 16 and vibration devices 18 disposed throughout and over the mask portion 12. As shown in FIG. 1, the LEDs can be placed evenly (or randomly and not evenly) anywhere within or between the dotted lines shown. Furthermore, the vibration devices 18 can be disposed in multiple places throughout the mask portion 12 to cause the mask portion to vibrate. FIG. 1 shows twelve vibration devices 18. However, anywhere between 1 and 100 or more vibration devices can be included. In some embodiments, the mask portion 12 may include a proximity sensor that detects the distance between the device and the user's face to dim and/or turn off the LED (or other treatment protocol) and to prevent eye safety or other skin safety issues or concerns. In some embodiments, the LEDs 16 may operate below a predetermined threshold (e.g., 20% power) when no face is detected by the proximity sensor. When the proximity sensor detects that a user's face is within a predetermined distance of the mask portion 12, then the mask portion 12 may activate the LEDs 16 to full treatment power.

As shown in FIG. 2, the mask system 10 can include a plurality of layers forming the mask portion 12. FIG. 2 shows three mask layers that include an inner layer 20, a middle layer 22 and an outer layer 24. In some embodiments, the LEDs 16 and the vibration devices 18 are connected to and powered by one or more flexible PCB members 26. The LEDs 16 and the vibration devices 18 can be on the same flexible PCB member(s) 26 or LEDs 16 and the vibration devices 18 can be on separate flexible PCB members 26. It will be appreciated that electrical connections are part of the flexible PCB member(s) 26 and connect the various LEDs 16 and vibration devices 18. The LEDs 16, the vibration devices 18 and flexible PCB member(s) 26 are referred to together herein as a therapy layer 27.

In some embodiments, the therapy layer 27 is secured between the inner and middle layers 20 and 22. The flexible PCB member 26 can be adhered or affixed to the inner surface of the middle layer 22 such that light from the LEDs is directed through the inner layer 20 and toward the wearer's skin. In an exemplary embodiment, the inner layer 20 can be made of silicone (other comfortable or rubber material), the middle layer 22 can be made of a thermoplastic elastomer (TPE) or other material, and the outer layer 24 can be made of polycarbonate (PC) or other rigid material to give shape to the mask portion 12.

In another embodiment, the therapy layer can be between the middle and outer layers or, when one or more middle layers are omitted, between the inner and outer layers. In another embodiment, the therapy layer can be disposed on the inner surface of the inner layer. It will be appreciated that two or more layers for the mask portion (or a single layer) are within the scope of the disclosure.

As shown in FIG. 2, in some embodiments, the mask system 10 includes a battery 28 and main PCB 30 secured on the outer surface of the outer layer 24 (e.g., on the forehead portion, but can be located elsewhere on the mask) that are secured by a housing or cap 32. In some embodiments, the cap 32 may be made of polycarbonate (PC). The mask system can also include a female jack for charging the battery and one or more switches or buttons for turning the lights and vibration devices on and off and/or changing speeds of the amplitude of the vibration devices or the intensity of the lights. The switch(es) can also be used to change between different light ranges or wavelengths for different treatments. FIG. 3 shows exemplary vibration devices 18 that could be used in the present disclosure.

Figure 4:
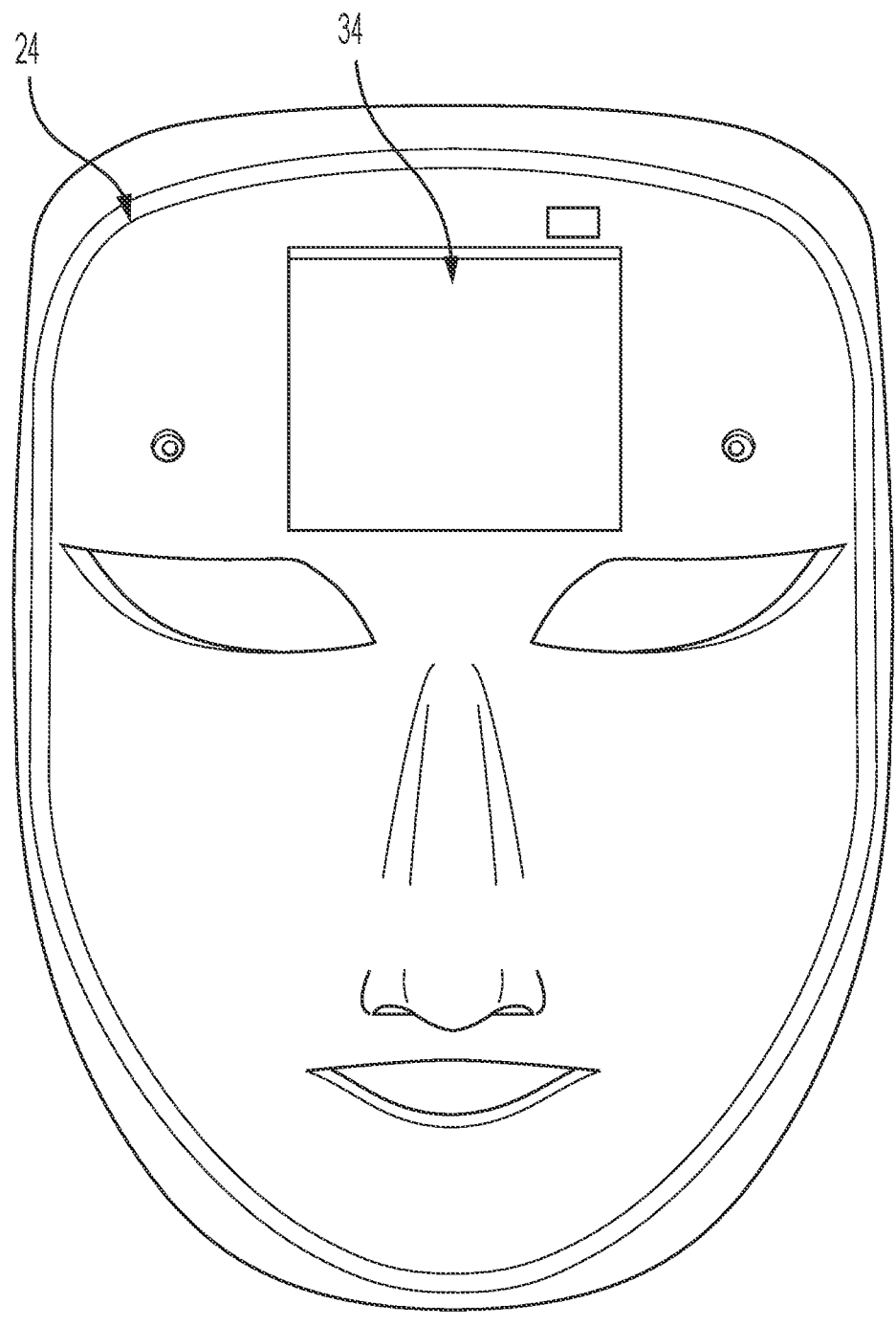
FIG. 4 illustrates an example diagram of an intermediate layer of a face mask, according to embodiments of the present disclosure.
Figure 5:
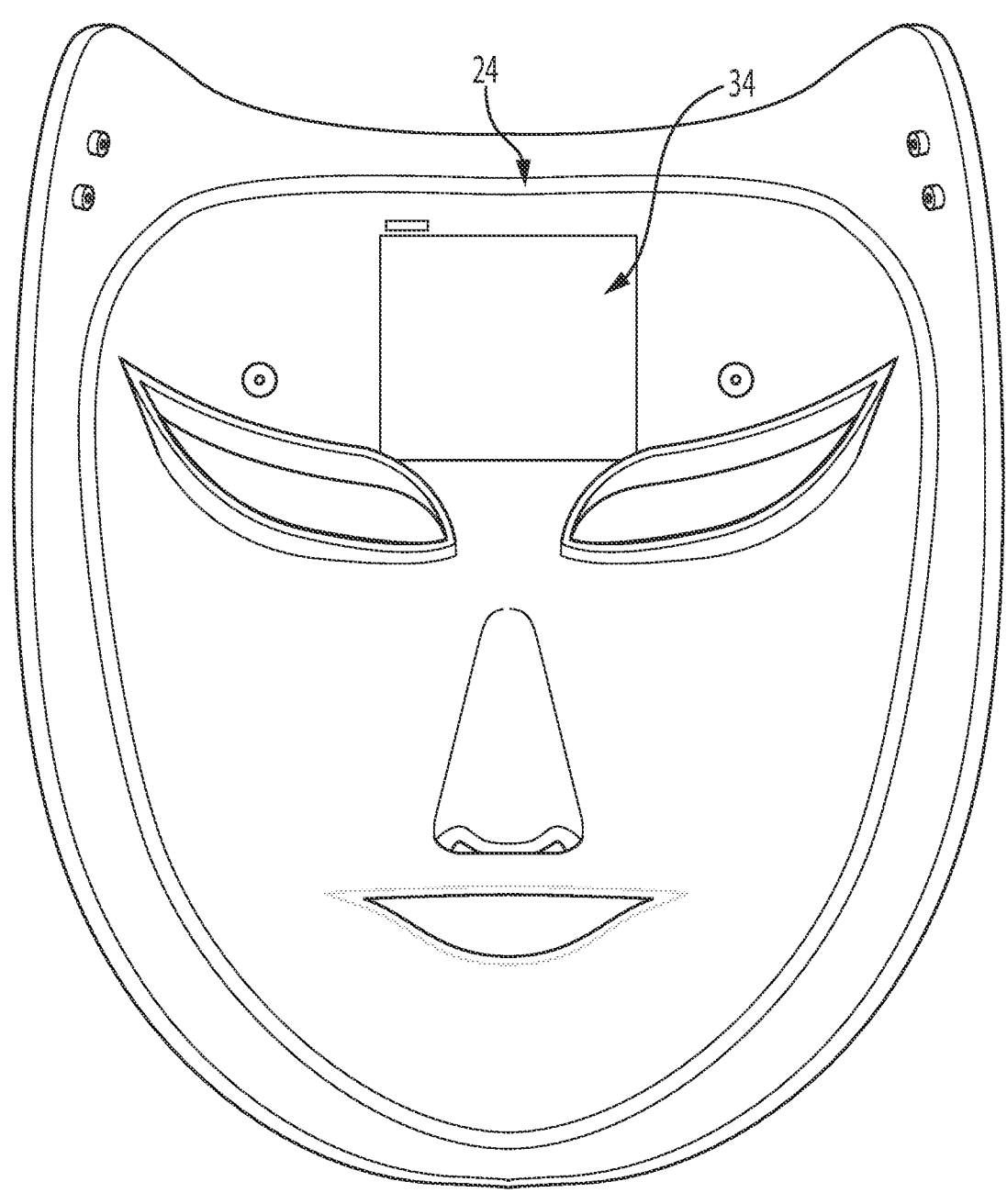
FIG. 5 illustrates an example diagram of an intermediate layer of a face mask, according to embodiments of the present disclosure.
Figure 6:
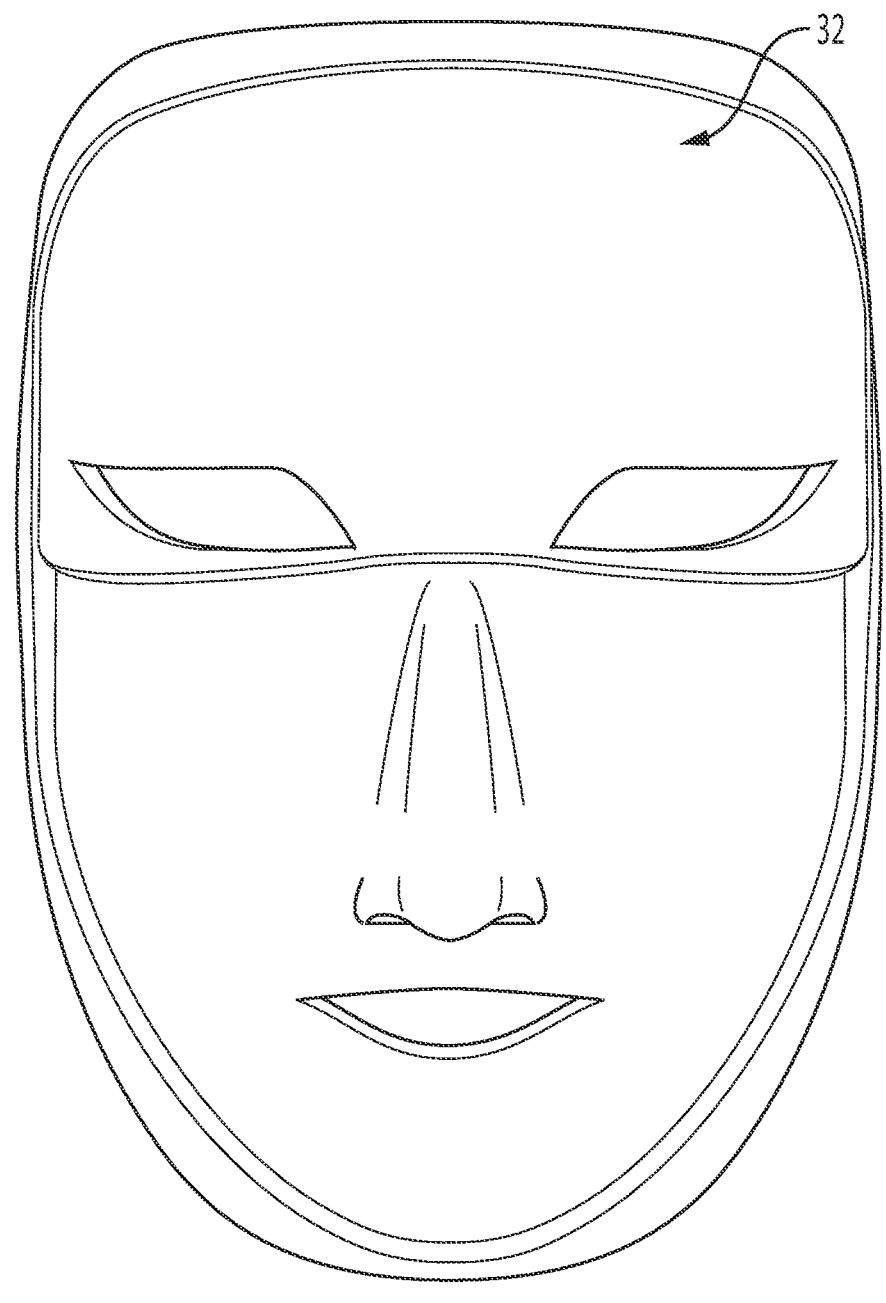
FIG. 6 illustrates an example diagram of an outermost or front layer of a face mask, according to embodiments of the present disclosure.
Figure 7:
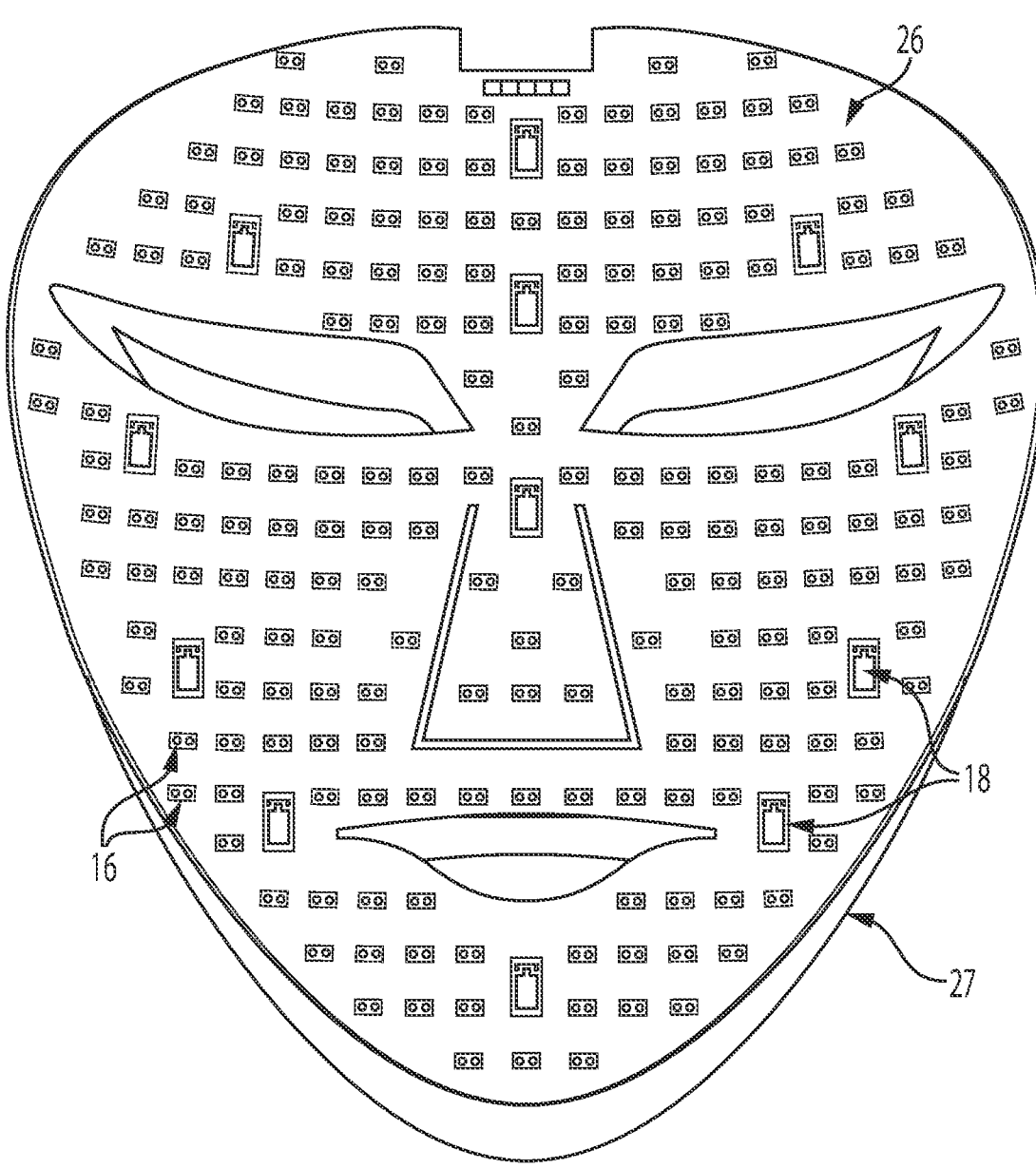
FIG. 7 illustrates an example diagram of a flexible PCB member with contacts for LED and vibration devices, according to embodiments of the present disclosure.
Figure 8:
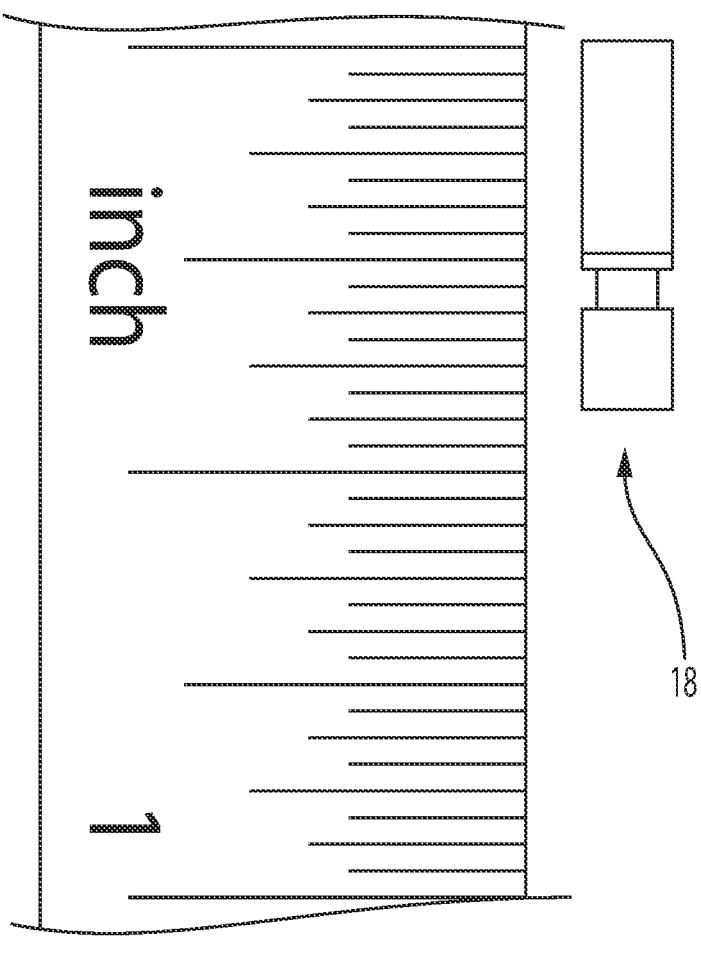
FIG. 8 illustrates an exemplary vibration device that can be used in the face mask, according to embodiments of the present disclosure.

FIGS. 4-7 show pictures of some embodiments of the disclosure. FIGS. 4-5 shows what is referred to above as the outer layer 24, but here is an intermediate layer 24 with a recess 34 for housing the battery 28 and main PCB 30. In this embodiment, instead of having a cover for the battery and PCB (or an addition to the cover) FIG. 6 shows an exemplary outermost or front layer of the mask system that acts as the cap 32 for the recess 34. FIG. 7 shows the flexible PCB member 26 with contacts showing where the LED 16 and vibration devices 18 (micro-motors) are electrically connected. FIG. 8 shows another exemplary vibration device 18 that can be used. Shown is a micro-motor with an eccentric weight that spins and causes vibration.

Figure 9:
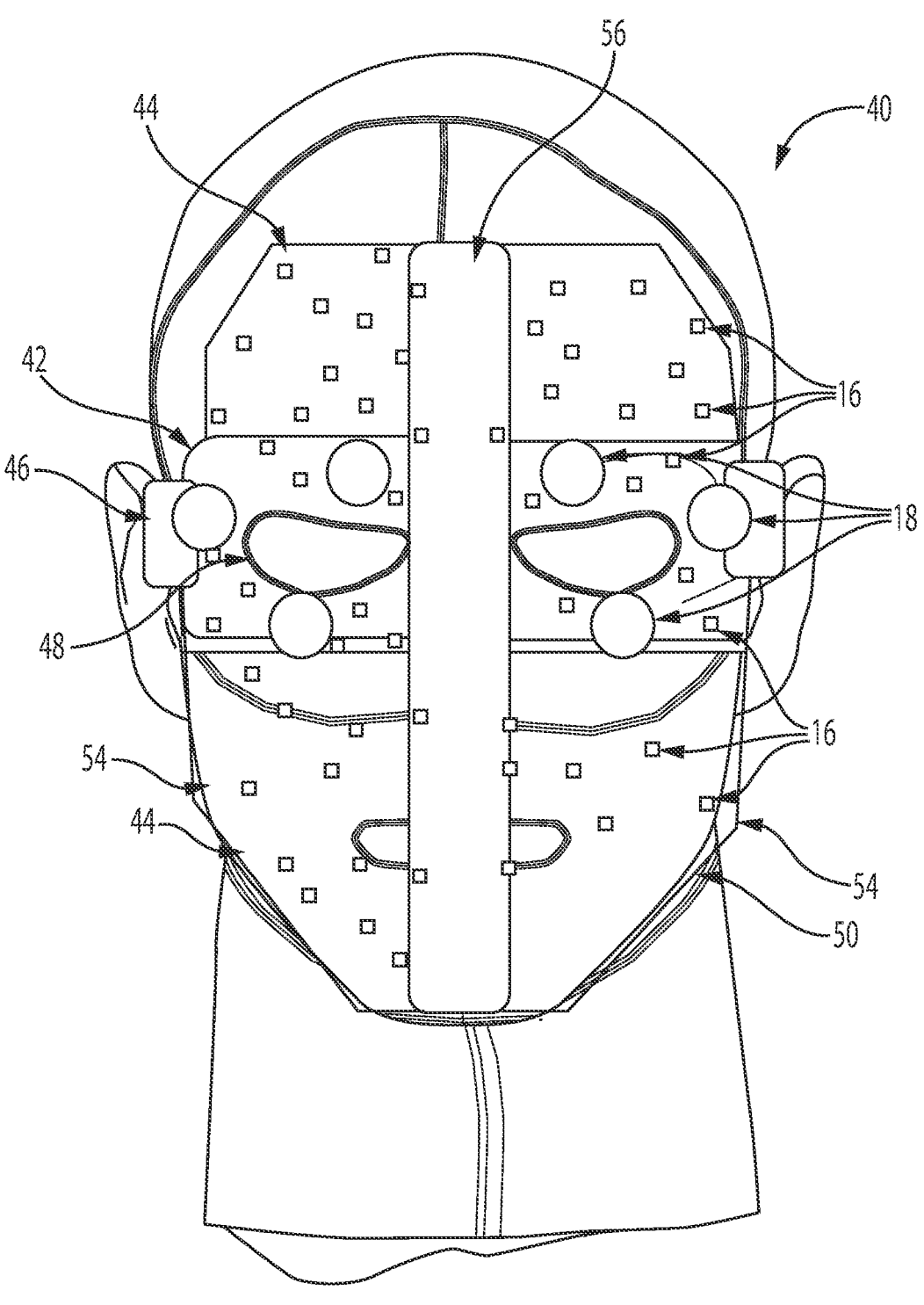
FIG. 9 illustrates an example diagram of a mask assembly configured on a user's face, according to embodiments of the present disclosure.

FIGS. 9-13 show a mask assembly 40 in accordance with some embodiments of the present disclosure. Generally, the mask assembly 40 includes an eye cover portion 42 and an extension portion 44. The eye cover portion 42 is similar to a set of goggles that cover and surround the eyes. As shown in FIG. 9, in some embodiments, the eye cover portion 42 includes vibration motors or devices 18 therein that provide vibration therapy to the area around the user's eyes (e.g., see the vibration devices in FIG. 3) and LEDs 16 that provide light therapy. In some embodiments, the vibration devices 18 are housed in a pocket 45 that extends outwardly from the eye cover portion 42 (extends further toward the wearer's skin than the remainder of the surface facing the wearer's skin) thus creating the contact points against the wearer's face. For example, if six vibration devices are included (as shown in FIG. 9), the six pockets, which can be made of a soft material, such as silicone, are the six points of contact against the user's skin. The LEDs 16 can be located anywhere within the eye cover portion 42, as shown in FIG. 9.

In some embodiments, the eye cover portion includes an outer cover or lens 48 that allows the user to see therethrough. In another embodiment, the outer cover or housing can include holes therein for the user to see through. In some embodiments, the device includes components therein (panels, deflectors, a channel or the like) that protect the wearer's eyes and prevent the LEDs from shining or emitting light into the wearer's eyes.

Figure 10:
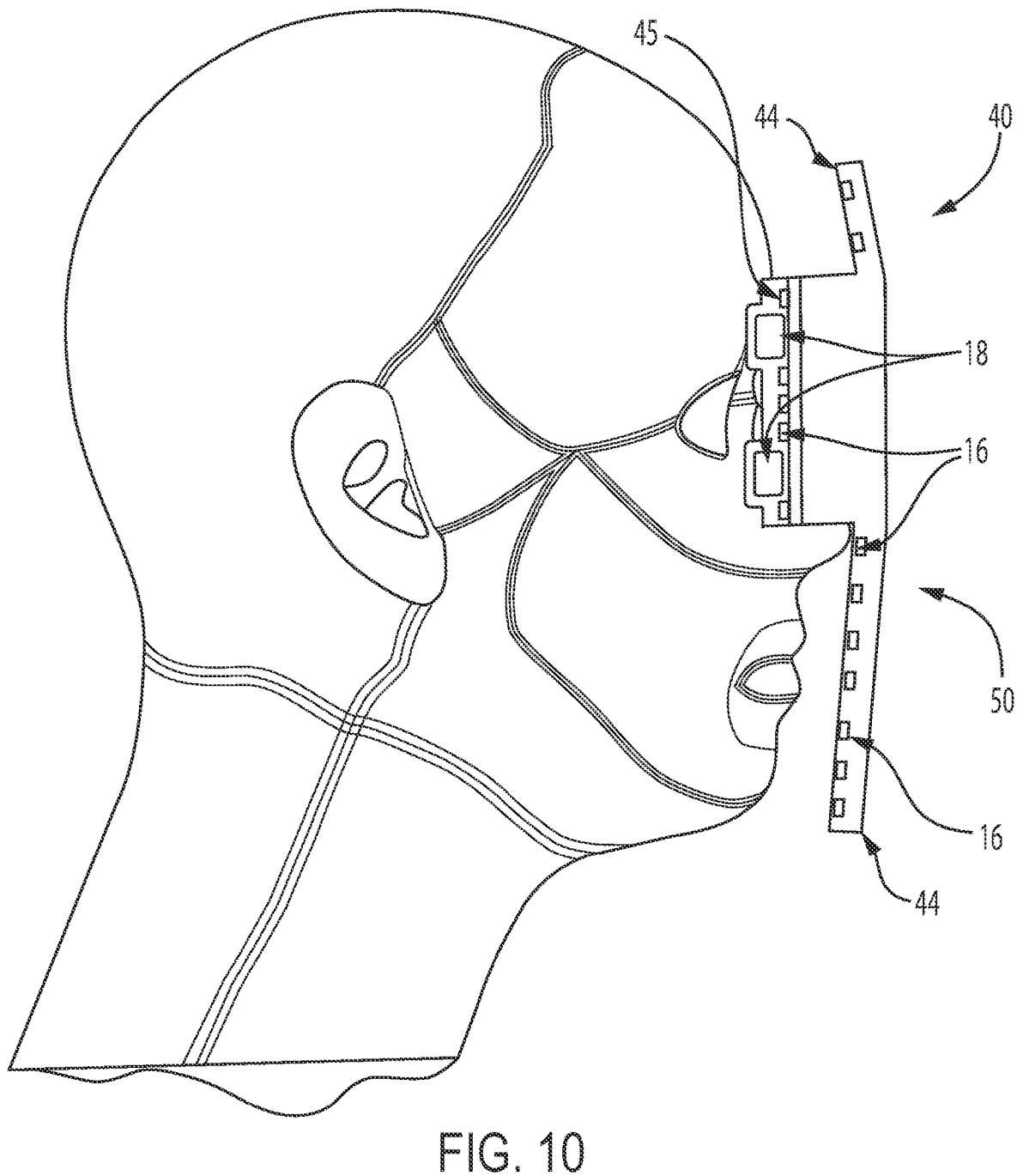
FIG. 10 illustrates a section view of a mask assembly configured on a user's face, according to embodiments of the present disclosure.

In some embodiments, the extension portion 44 includes LEDs 16 that provide light therapy, but does not include vibration devices. As shown in FIG. 10, the extension portion 44 is spaced or offset from and does not contact the wearer's face or skin. For example, the extension portion(s) 44 may be spaced 2-3 cm from the face of the user. As a result, the only point of contact with the wearer's face or skin (other than the strap 46 holding the device on) is around the eye area (by the eye cover portion 42). The extension portion 44 provides the ability to increase the treatment area of the LEDs from just the areas around the eyes. In some embodiments, the extension portion 44 extends upwardly to at least partially cover the forehead and down to at least partially cover the lower half of the face. In another embodiment, portions of the extension portion may contact the wearer's face. As shown in FIG. 10, in some embodiments, the extension portion(s) 44 include a housing 50 having an interior portion that is transparent to allow the LEDs 16 to shine therethrough. The housing 50 houses the LEDs and the PCB necessary therefore.

In some embodiments, the mask assembly 40 includes a power source, such as a rechargeable battery and the requisite electronics, such as a controller, PCB, user interface, buttons, etc. In some embodiments, these components are located within the eye cover portion.

Figure 11:
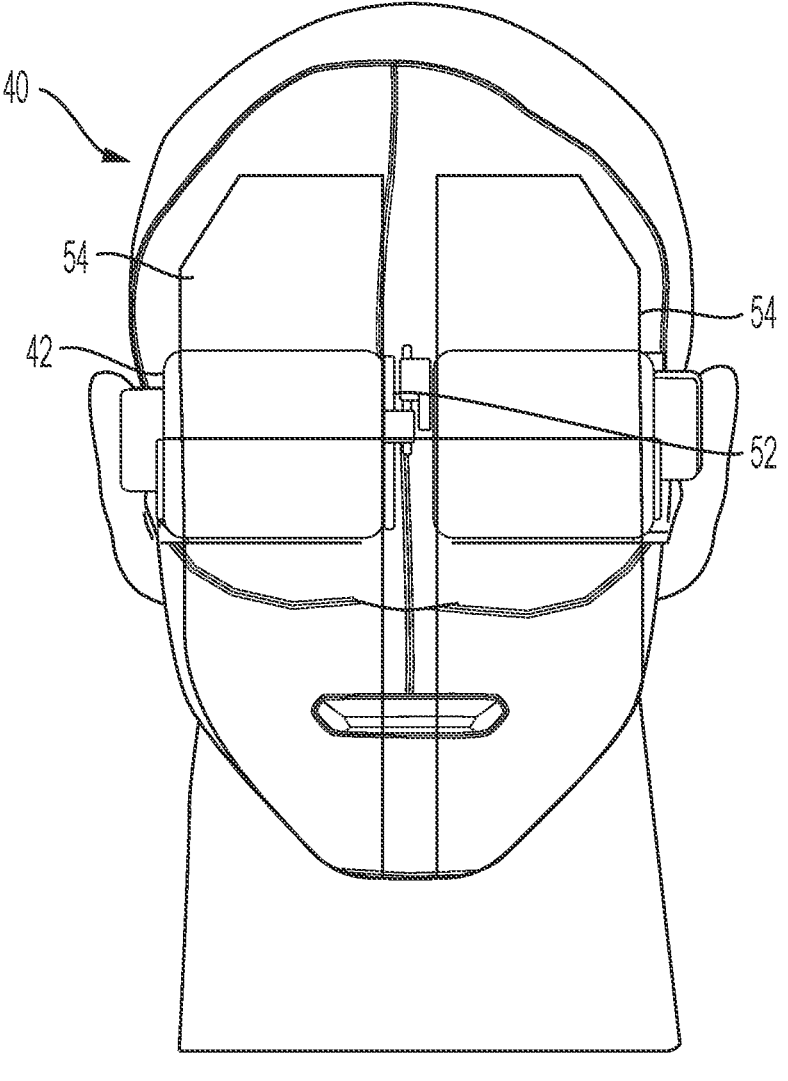
FIG. 11 illustrates an example diagram showing a hinge in the mask assembly, according to embodiments of the present disclosure.
Figure 12:
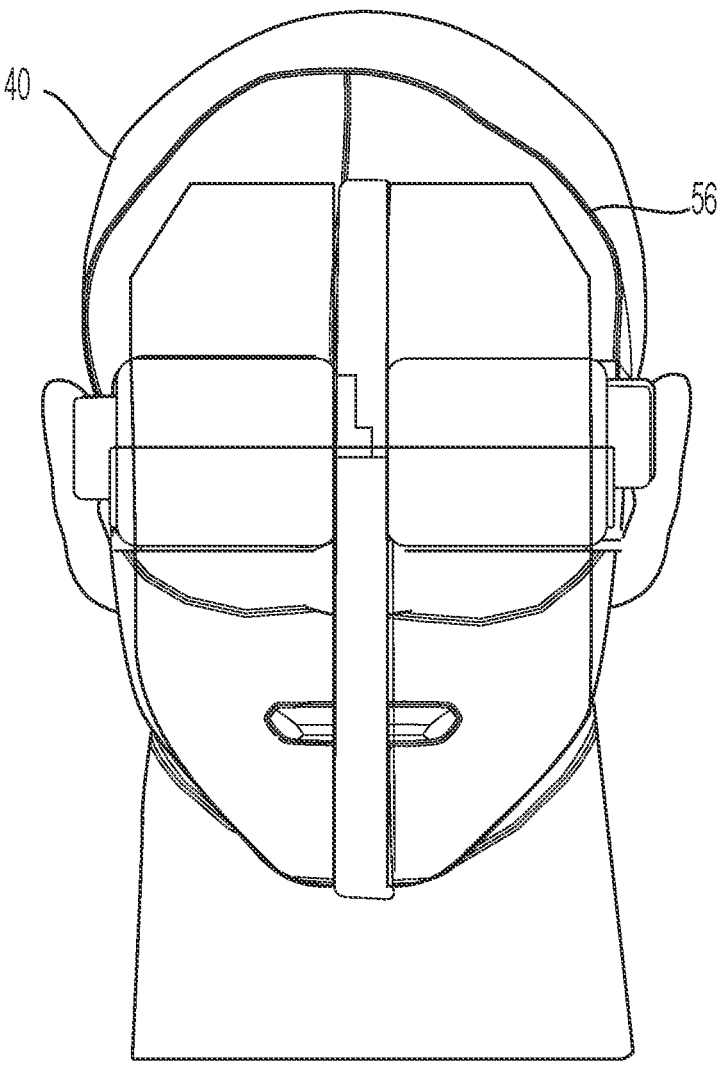
FIG. 12 illustrates an example diagram of cover arranged on top of the hinge in the mask assembly, according to embodiments of the present disclosure.
Figure 13:
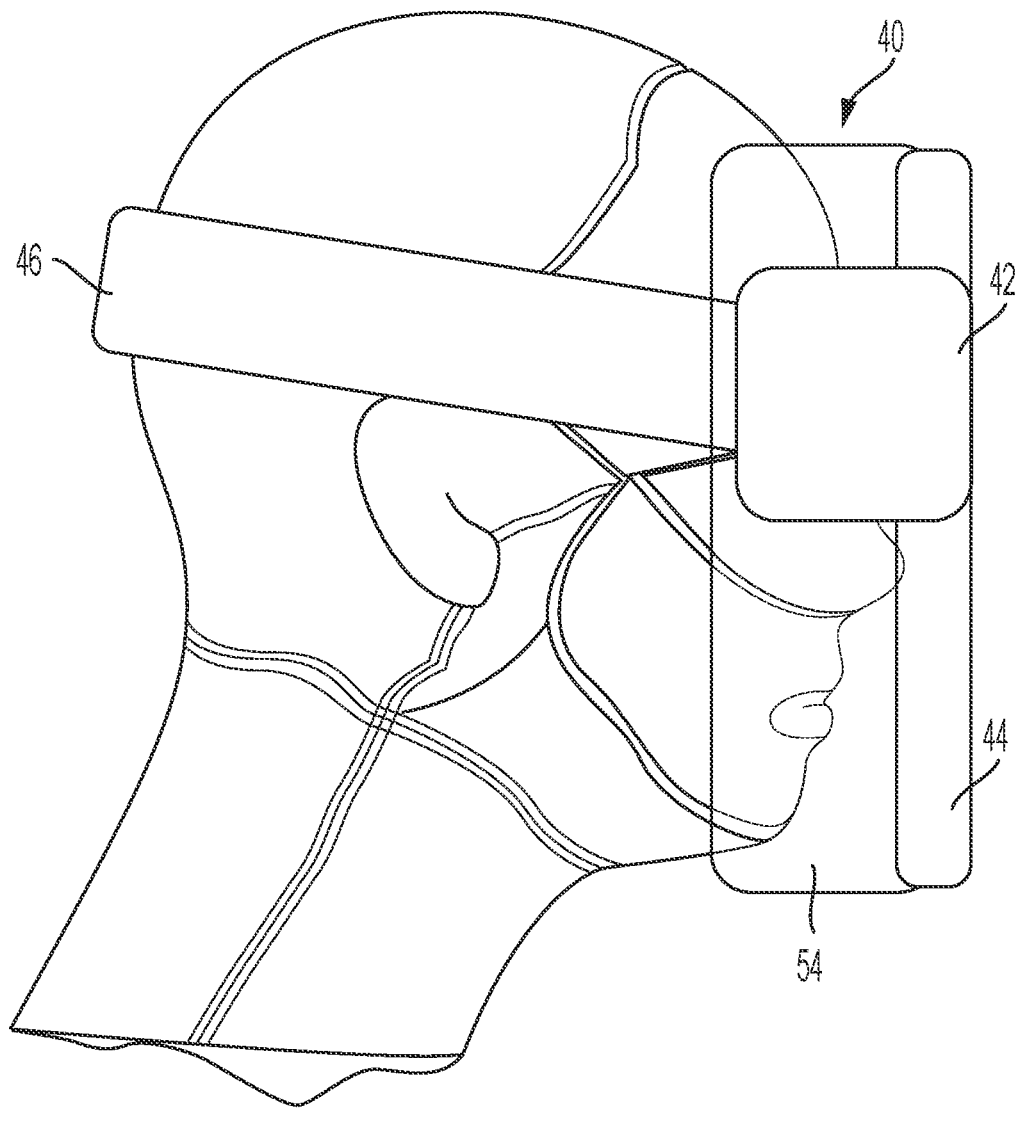
FIG. 13 illustrates an example diagram showing a side view of the mask assembly and a strap coupled to the mask assembly, according to embodiments of the present disclosure.

As shown in FIGS. 11-13, in some embodiments, the mask assembly 40 includes a hinge assembly 52 extending vertically along the center of the mask to allow one or both of the eye cover portion 42 and the extension portion 44 and the housings and other components thereof to expand outwardly or inwardly so that the device can adapt to fit on different wearer's heads (that are sized differently). The hinge assembly 52 allows the two outer panels 54 to move outwardly (to fit a larger head/face) or inwardly (to fit a smaller head/face). In some embodiments, the device includes a hinge cover 56 for covering and hiding the hinge assembly 52.

Figure 14A:
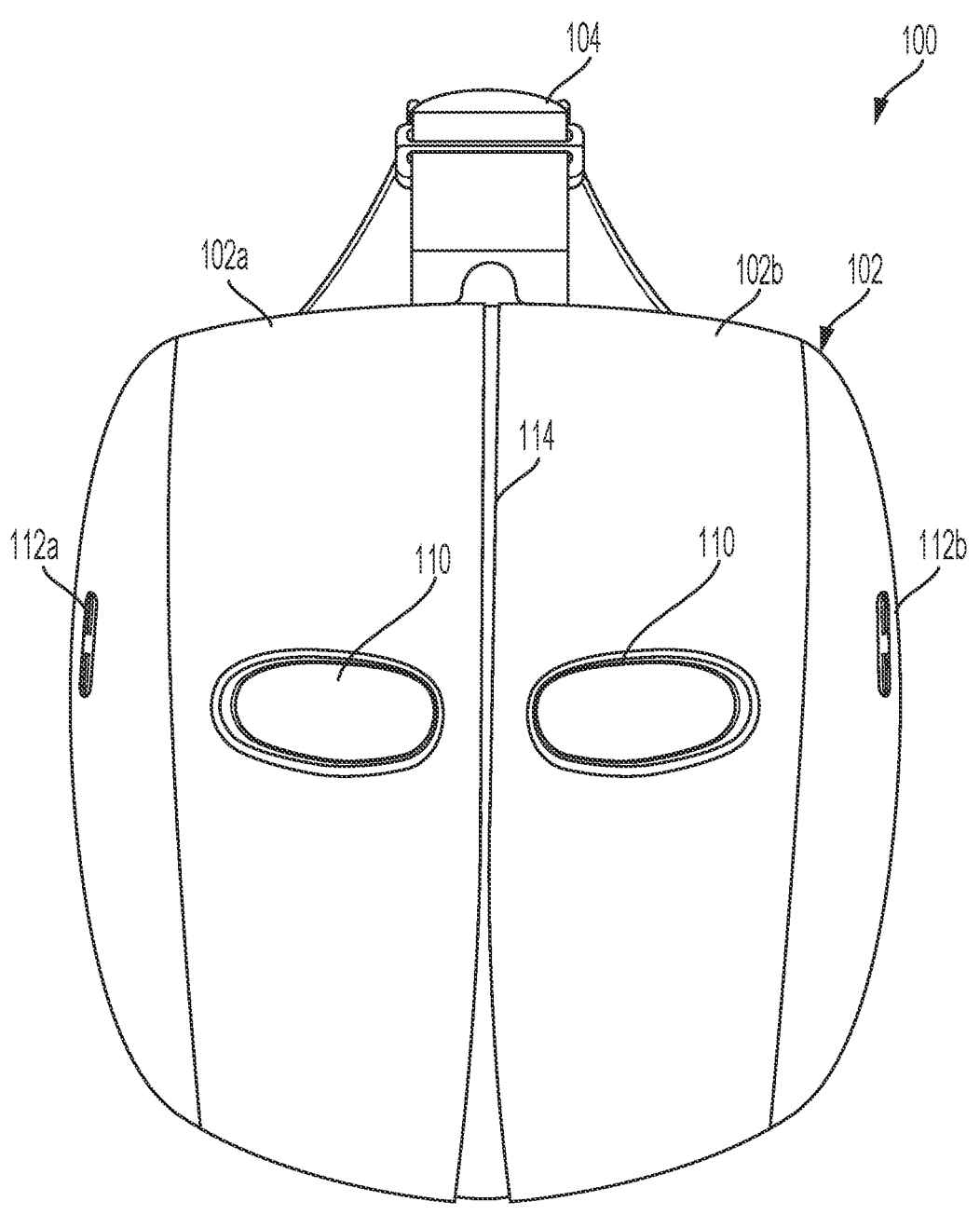
FIG. 14A illustrates a front view of a mask assembly, according to embodiments of the present disclosure.

FIG. 14A illustrates a front view of a mask assembly 100, according to embodiments of the present disclosure. In some embodiments, the mask assembly 100 may be referred to herein as a mask apparatus, mask system, face mask, or the like. The mask assembly 100 includes a mask portion 102 and a strap 104 coupled to the top of the mask portion 102. The mask portion 102 includes a first panel 102a and a second panel 102b with a hinge 114 arranged in the center between the first and second panels 102a and 102b. In some embodiments, the hinge 114 may be arranged along a longitudinal axis at the center of the mask portion 102 in between the first and second panels 102a and 102b. The hinge 114 allows movement and adjustment of the first and second panels 102a and 102b to fit on different wearer's heads (that are sized differently). For example, a user wearing the mask assembly 100 can adjust the distance of the first and second panels 102a and 102b from the hinge 114 according to the user's head size. In some embodiments, the first and second panels 102a and 102b may be referred to herein as first and second outer panels. The mask portion 102 includes openings 110 configured to fit over a user's eyes when wearing the mask assembly 100. A first opening 110 may be arranged in the middle of the first panel 102a, and a second opening 110 may be arranged in the middle of the second panel 102b.

The mask portion 102 may include one or more buttons 112 for controlling operations and different modalities of the mask assembly 100. The one or more buttons 112 may include a first button 112a and a second button 112b, both located on an outward-facing side of the mask portion 102.

First button 112a may be located on an external side of the first panel 102a and may control operation of LED lights in the mask assembly 100. Second button 112b may be located on an external side of the second panel 102a and may control operation of vibration motors in the mask assembly 100. In some embodiments, a wearer or user of the mask assembly 100 may utilize the first and second buttons 112a and 112b to control settings of the mask assembly 100 and/or to execute different protocols associated with the LED lights and/or vibration motors. In some embodiments, the user of the mask assembly 100 may press the first and/or second buttons 112a and 112b to switch on/off a subset or all of the vibration motors and/or LED lights, change the speed of the vibration motors, change the color and/or brightness of the LED lights, or the like. In some embodiments, the LED lights in the mask assembly 100 may have different modes, such as flashing, or operating at different patterns, such as a wave pattern. In some embodiments, the vibration motors in the mask assembly 100 may have similar modes as the LED lights and may also operate at different patterns as selected by the user. In some embodiments, the user may use the first and/or second buttons 112a and 112b to select from different protocols that combine LED light and vibration therapy according to the user's preferences. In some embodiments, the mask portion 102 may also include one or more LED indicators to show power, charging, and/or Bluetooth or connectivity statuses of the mask to a user.

Figure 14B:
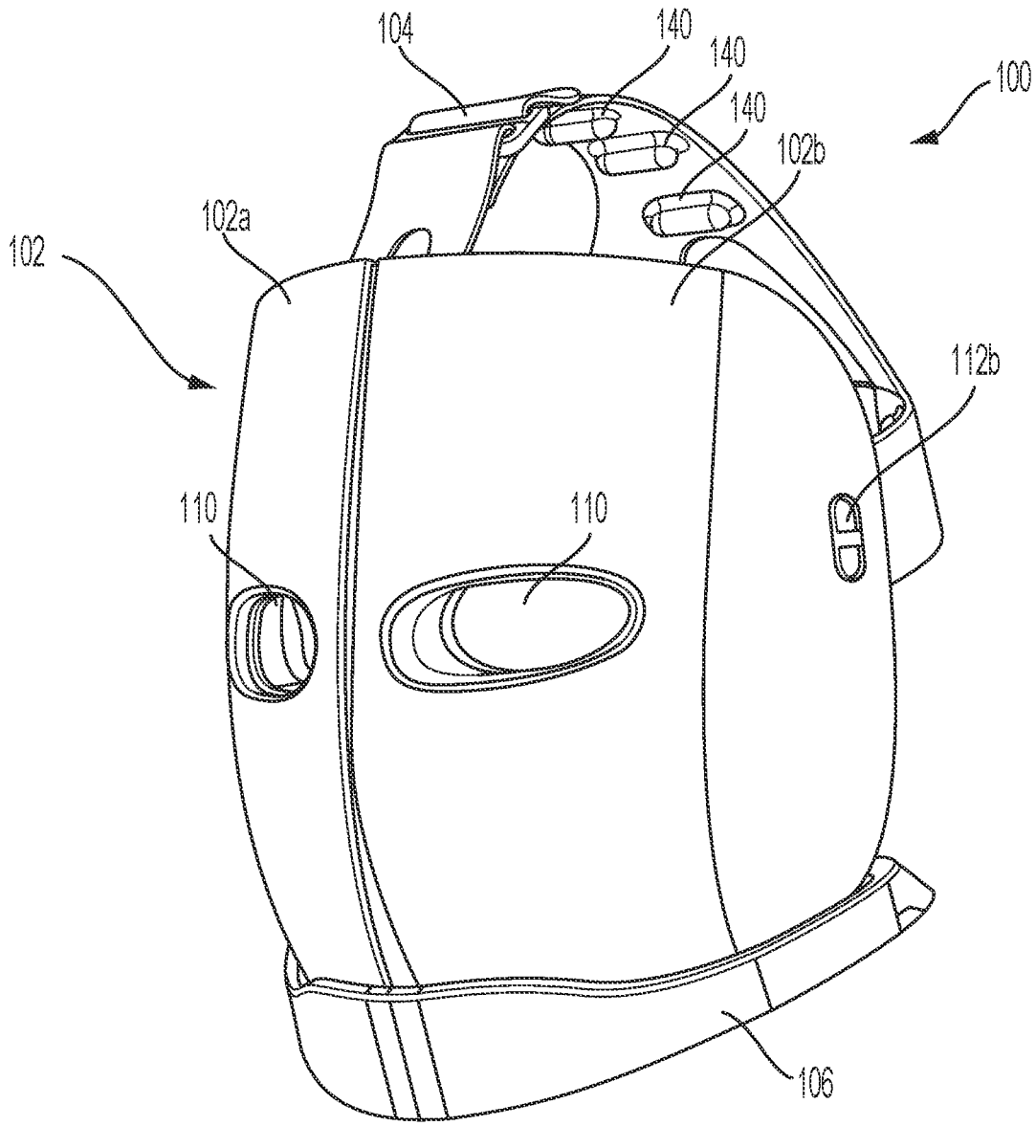
FIG. 14B illustrates a perspective view of the mask assembly, according to embodiments of the present disclosure.

FIG. 14B illustrates a perspective view of the mask assembly 100, according to embodiments of the present disclosure. In particular, FIG. 14B shows the mask assembly 100 arranged in a stand 106. The stand 106 may be configured to receive a bottom portion or chin area of the mask portion 102. In some embodiments, the stand 106 may include one or more openings, slots, or grooves that are designed to secure or hold the bottom portion or chin area of the mask portion 102. A user may retrieve the mask assembly 100 from the stand 106 for using the LED and vibration treatment and then mount the mask assembly 100 in the stand 106 after use. FIG. 14B also shows the inner portion of the strap 104, and vibration motors 140 that are arranged on the inner portion of the strap 104. Vibration motors 140 may be pill-shaped motors that are configured to provide vibration therapy to a user's head while wearing the strap 104 and mask assembly 100. While FIG. 14B shows three vibration motors 140 in the strap 104, there may be any number of vibration motors 140 arranged in one or more different locations in the strap 104.

Figure 15:
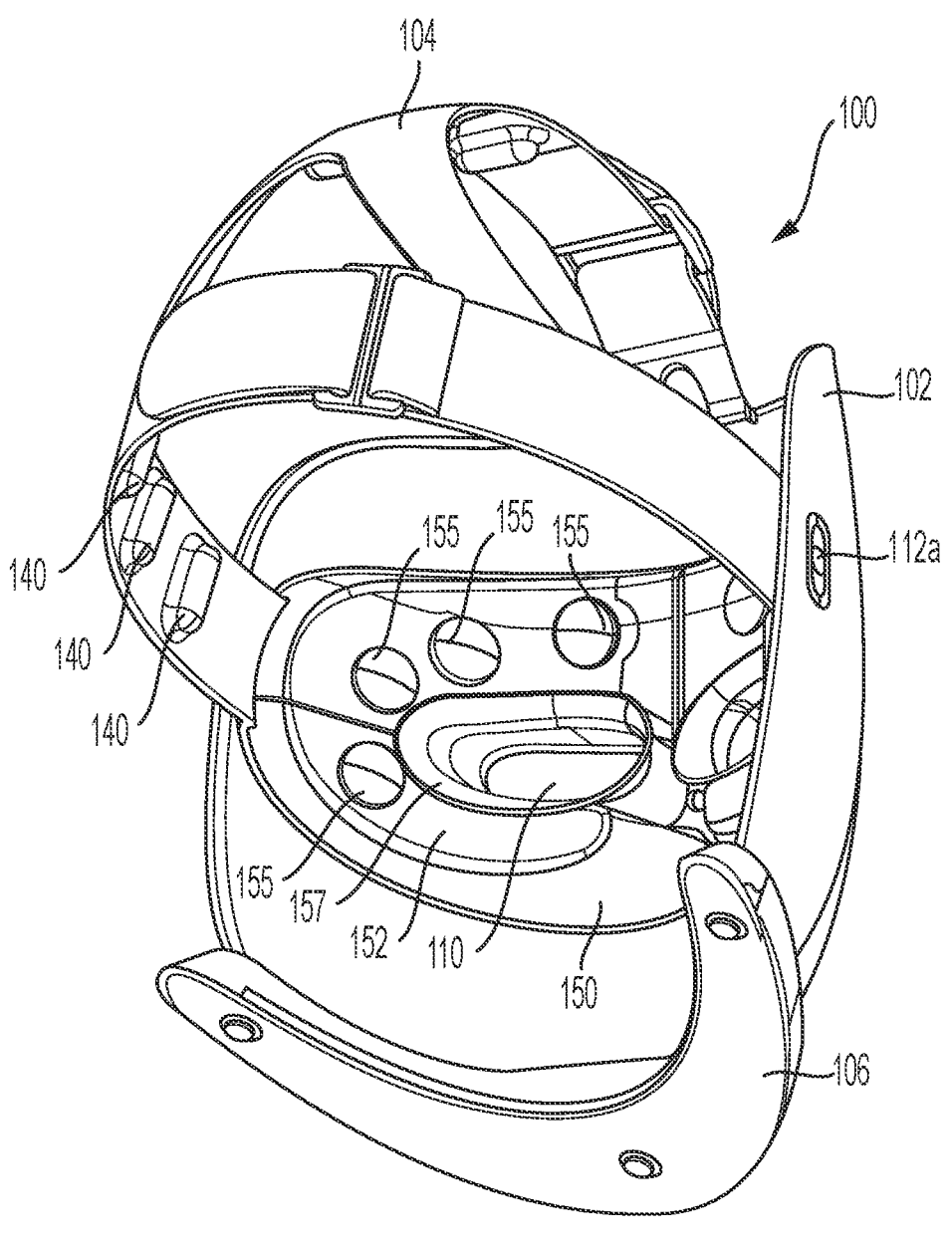
FIG. 15 illustrates a perspective inner view of the mask assembly, according to embodiments of the present disclosure.

FIG. 15 illustrates a perspective inner view of the mask assembly 100, according to embodiments of the present disclosure. In some embodiments, FIG. 15 shows the side of the mask portion 102 that is arranged over a user's face and an eye portion 150. Eye portion 150 may be coupled to a silicone mask layer of the mask (e.g., a mask layer facing the user's skin when wearing the device). Eye portion 150 includes a silicone layer 152 that is configured to cover an area around the user's eyes. In some embodiments, the silicone layer 152 of the eye portion covers at least partially the area around the user's forehead, eyebrows, cheekbones, and/or temples. In some embodiments, the silicone layer 152 may be a silicone cap that is translucent and provides a flexible and comfortable material to rest of the user's face when wearing the mask assembly 100.

The eye portion 150 further includes vibration motors 155 that are encapsulated in the silicone layer 152. The silicone layer 152 may include a plurality of molded slots that are configured to hold the vibration motors 155 in place. In some embodiments, vibration motors 155 may be coin motors and/or eccentric rotating mass (ERM) motors that are configured to provide vibration therapy to the user. In some embodiments, the vibration motors 155 may be referred to herein as vibration devices or motors. In some embodiments, the silicone layer 152 may provide a raised edge that allows the vibration motors 155 and the eye portion 150 to rest comfortably on the user's face when wearing the mask assembly 100. In some embodiments, the silicone layer 152 may provide a noise dampening functionality to dampen any noise from the vibration motors 155. While FIGS. 15-18 shows four vibration motors 155 arranged each opening 110 in the mask portion 102, there may be any number of vibration motors 155 arranged in the eye portion 150.

The eye portion 150 may be arranged over a user's eyes and adjusted via the strap 104. In some embodiments, the strap 104 may be coupled to the sides of the eye portion 150. In some embodiments, the strap 104 may comprise one or more elastic bands, nylon bands, or the like. In some embodiments, the strap 104 may be adjustable to the user's head via one or more buckles. The strap 104 may include a top portion that is in contact with the top of a user's head, and a bottom portion that extends laterally from the sides of the user's head. In some embodiments, the top portion of the strap 104 may extend along a longitudinal plane or sagittal plane of the user's head. In some embodiments, the bottom portion of the strap 104 may extend along a lateral plane or transverse plane of the user's head. In some embodiments, the bottom portion of the strap 104 may be referred to herein as a lateral portion of the strap. In some embodiments, the strap 104 may include one or more bands and one or more buckles used to fasten or secure the one or more bands around the user's head.

In some embodiments, the different vibration motors (vibration motors 155 and vibration motors 140) in mask assembly 100 may be utilized to provide vibration therapy in different zones or areas of the user's head and face. In some embodiments, the vibration motors 155 may provide vibration therapy to areas around a user's eyebrows, cheekbones, and the like. In some embodiments, the vibration motors 155 and 140 may be activated to provide vibration therapy in a wave sequence of vibration that goes from applying vibration at the front of the foreheads, to eyebrows to cheeks to temples (e.g., via the vibration motors 155 in the eye portion, to ears, and around the user's head (via the vibration motors 140 in the strap 104). In some embodiments, the user may select which area in the mask assembly 100 to provide vibration therapy, and may turn on/off one or more of the vibration motors 155 and vibration motors 140 separately or in combination.

Figure 16:
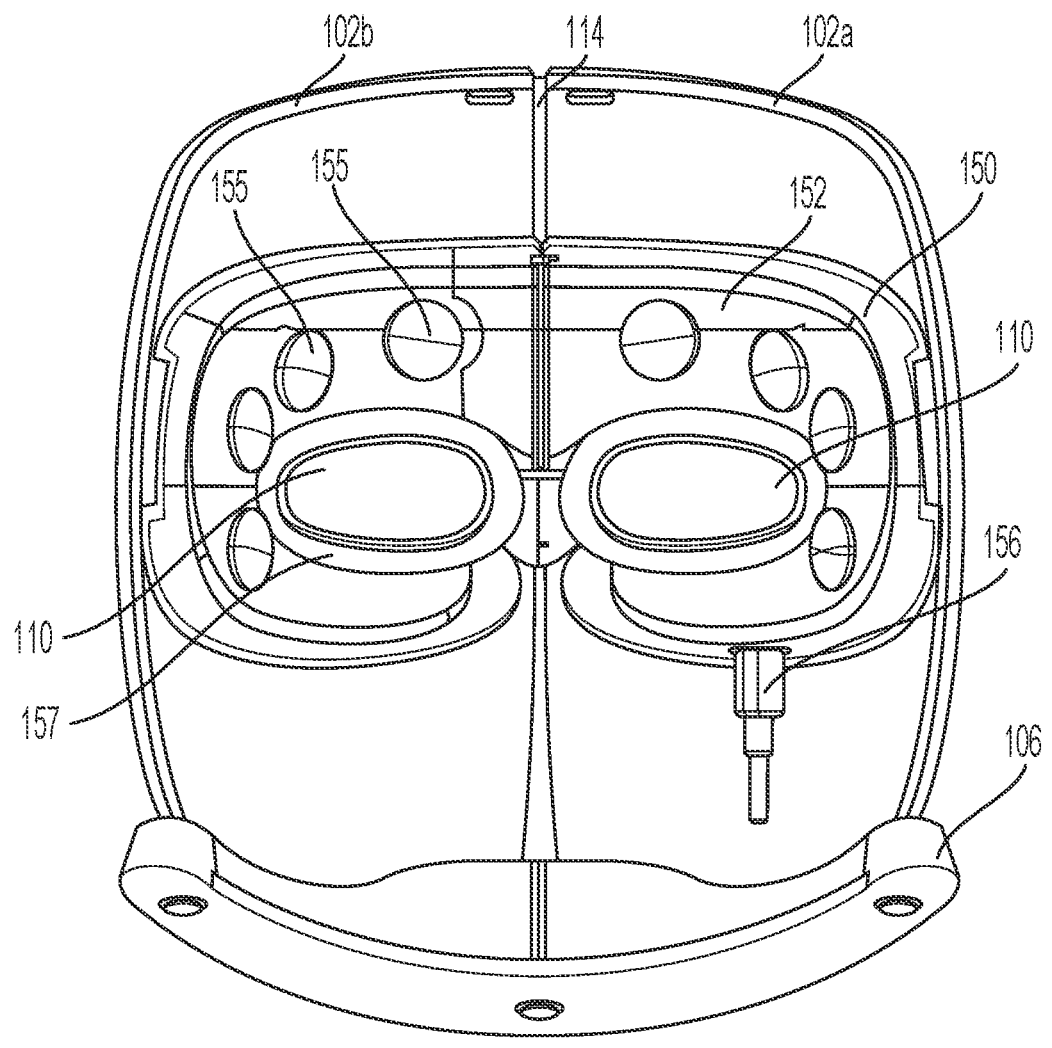
FIG. 16 illustrates an inner view of the mask assembly without the strap, according to embodiments of the present disclosure.

FIG. 16 illustrates an inner view of the mask assembly 100 without the strap 104, according to embodiments of the present disclosure. FIG. 16 shows the eye portion 150 and the placement of the vibration motors 155 in the silicone layer 152. The inner view in FIG. 16 also illustrates an internal connection port 156 that allows electrical connection to the vibration motors 155, LEDs, and electronics in the mask assembly 100. In some embodiments, the internal connection port 156 may also provide a USB connection for charging the mask assembly 100.

In some embodiments, FIGS. 15 and 16 show the mask assembly 100 coupled to the stand 106, and a removable eye cover 157. In some embodiments, the removable eye cover 157 may be inserted in an area next to the silicone layer 152. In some embodiments, the removable eye cover may be adjacent to the space of the openings 110 of the mask portion 102. In some embodiments, the removable eye cover 157 may be made of silicone. In some embodiments, the removable eye cover 157 may help block light (e.g., light from the LEDs in the mask) from the user's eyes when wearing/using the mask.

Figure 17:
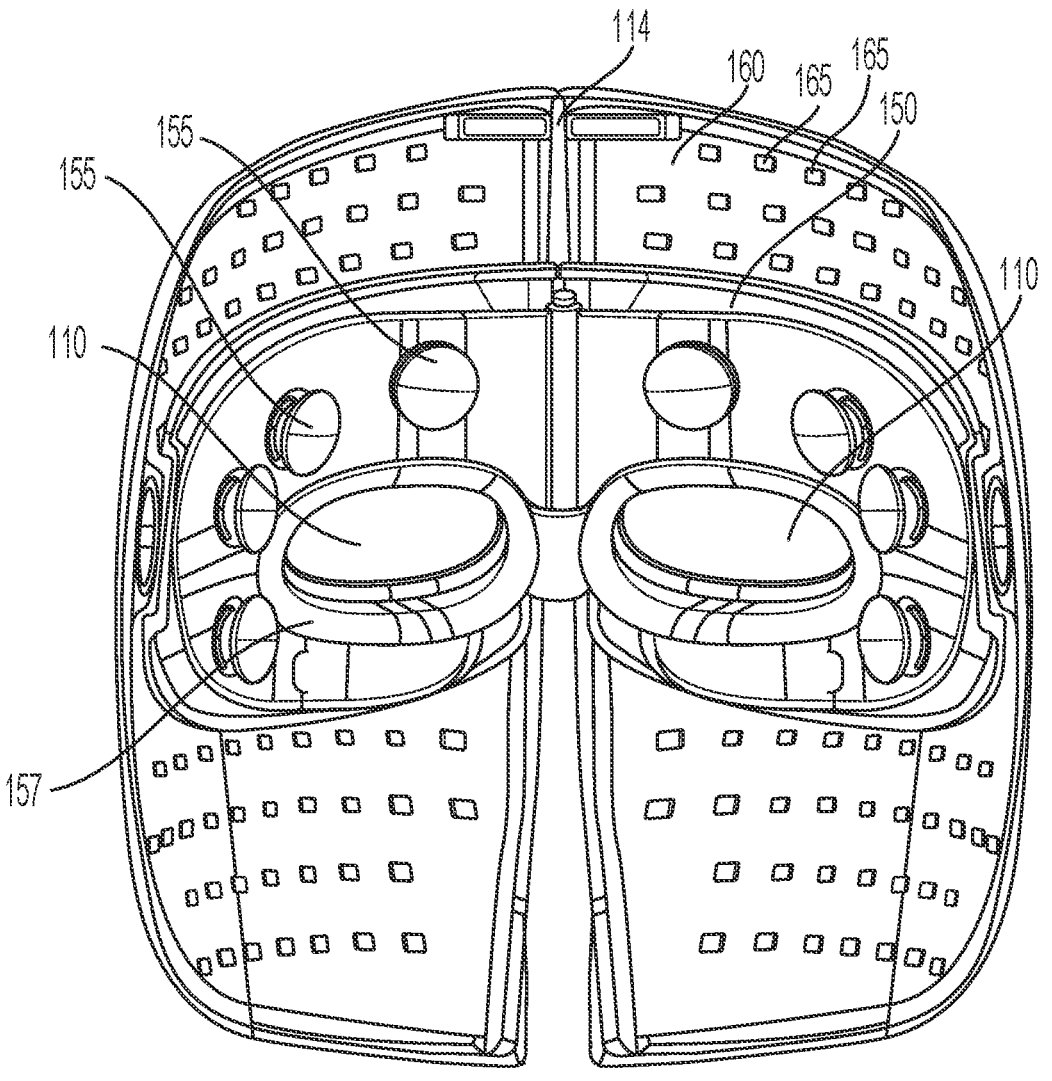
FIG. 17 illustrates an inner view of an LED layer of the mask assembly, according to embodiments of the present disclosure.

FIG. 17 illustrates an inner view of an LED layer 160 of the mask assembly 100, according to embodiments of the present disclosure. In some embodiments, the LED layer 160 may be referred to herein as a middle layer of the mask. In some embodiments, the LED layer 160 may comprise one or more layers that are arranged as middle layers in the mask portion 102. In some embodiments, there may be multiple middle layers or additional silicone layers that are arranged adjacent to the LED layer 160. In some embodiments, the LED layer 160 may comprise a plurality of LEDs 165 that are configured to provide light therapy to a user's face. In some embodiments, the plurality of LEDs 165 may be configured to emit at least one of a red light, blue light, infrared (IR) light, or any combination thereof. In some embodiments, the red light may have an emittance in a range of 68 mW-78 mW and a peak wavelength in a range of 623 nm-643 nm, the blue light may have an emittance of 45 mW-55 mW and a peak wavelength of 405 nm-425 nm, and the IR light an emittance of 50 mW-60 mW and a peak wavelength of 820 nm-840 nm. In some embodiments, a silicone layer may be arranged on top of the LED layer 160 to provide a comfortable layer to rest on the user's face when wearing the mask. In some embodiments, the silicone layer may be optically transparent, such that light from the LEDs 165 can be emitted through the silicone layer to treat the user's skin.

Figure 18:
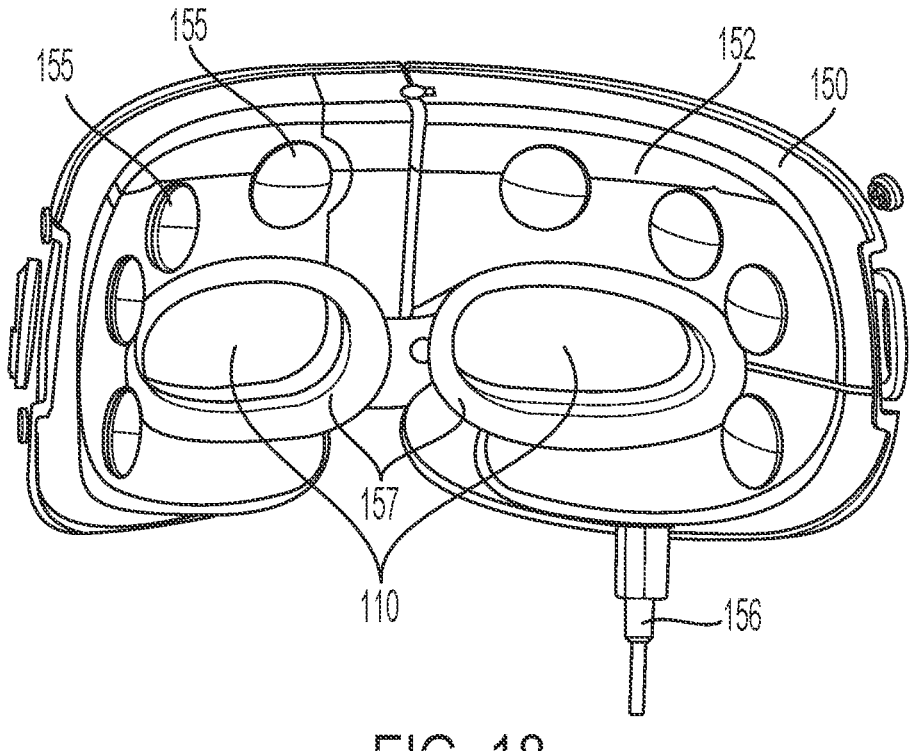
FIG. 18 illustrates an inner view of the eye portion of the mask assembly, according to embodiments of the present disclosure.

FIG. 18 illustrates an inner view of the eye portion 150 of the mask assembly, according to embodiments of the present disclosure. In some embodiments, FIG. 18 illustrates the eye portion 150 of the mask assembly 100 without being coupled to the strap 104 or the stand 106. In some embodiments, the eye portion 150 may include fasteners and other components that allow the eye portion 150 to be affixed to the different structures and layers in the mask assembly 100.

Figure 19:
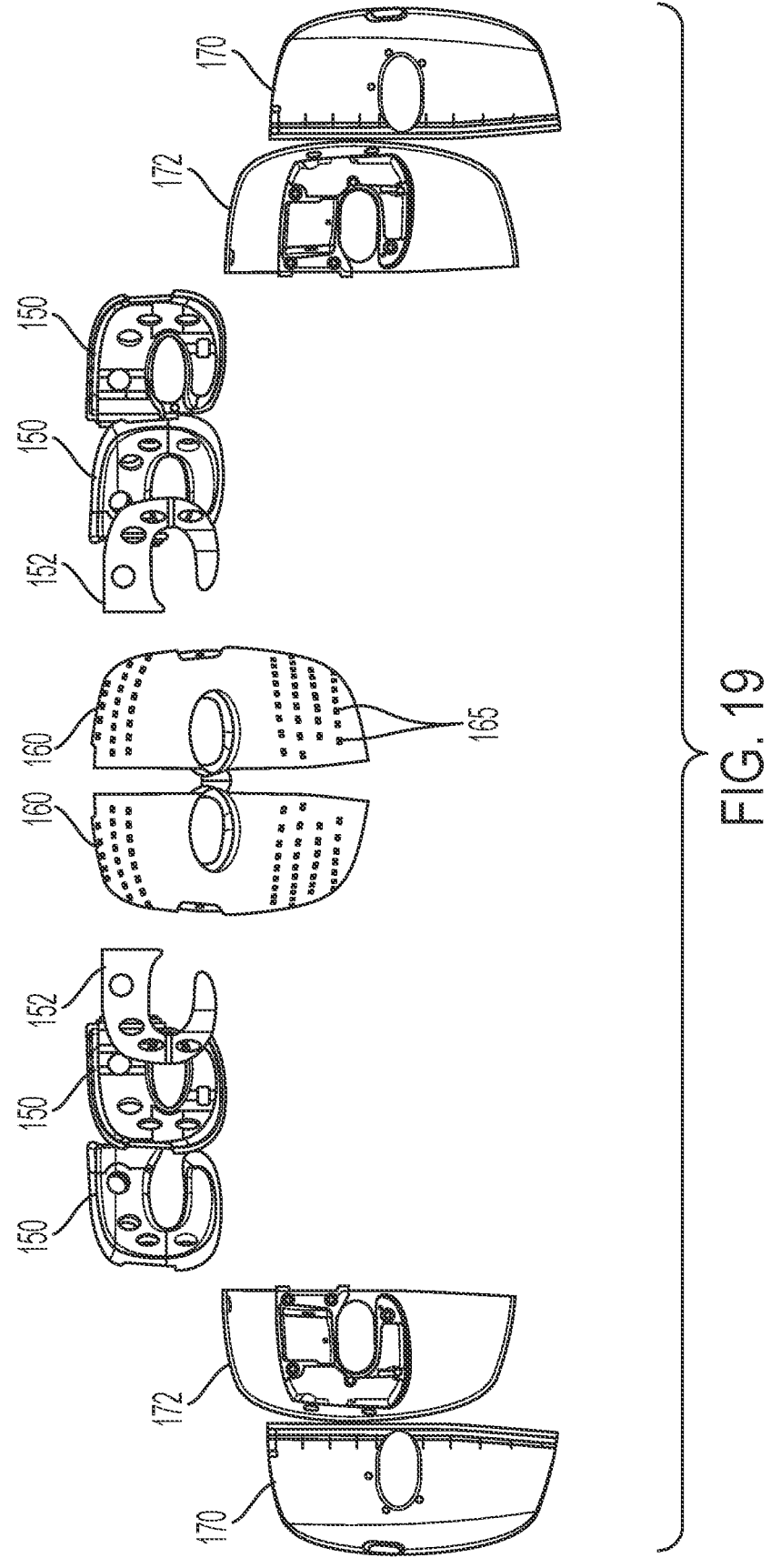
FIG. 19 illustrates an exploded inner view of the components of the mask assembly, according to embodiments of the present disclosure.

FIG. 19 illustrates an exploded inner view of the components of the mask assembly 100, according to embodiments of the present disclosure. In some embodiments, the mask portion 102 may include multiple layers, including an outer layer 170, an LED layer 160, and an inner layer 172. In some embodiments, the outer layer 170 may comprise polycarbonate (PC) and may include the outer shell that points away from the user's face when wearing the mask assembly 100.

In some embodiments, the outer layer 170 may include an inner shell that has housing configured to hold the electronic components, battery, wiring, and the like. The LED layer 160 may be mounted on the inside of the outer layer 170 (e.g., on the side of the outer layer 170 that faces the user wearing the mask). In some embodiments, the LED layer 160 may be made of a thermoplastic elastomer (TPE) and may also include one or more PCB members for powering the LEDs and vibration motors 140, 155 in the mask. In some embodiments, the LED layer 160 may comprise one or more middle layers that may include one or more sensors and/or other components configured to improve vibration and/or comfort for the user wearing the mask. In some embodiments, one or more middle layers (or other components) in the mask assembly 100 may include one or more electrocardiogramaensors, electroencephalography (EEG) sensors, photoplethysmography (PPG) sensors, or other biometric sensors that are configured to obtain measurements of a user of the mask. In some embodiments, the LEDs, vibration motors, and/or sensors may be housed in one or more PCB members that are also in electrical and/or data communication with the vibration motors, control modules for the mask, and the like.

In some embodiments, the inner layer 172 may made of silicone or a rubber material and may include structural components for housing components of the eye portion 150. FIG. 19 shows the layers of the eye portion 150 and the silicone layer 152, which may fit in the housing built in the inner layer 172. In some embodiments, the eye portion 50 may comprise one or more layers, including structural components and housing for the vibration motors 155. In some embodiments, the layers of the eye portion 150 and silicone layer 152 may each include openings that are configured to receive vibration motors 150.

Figure 20:
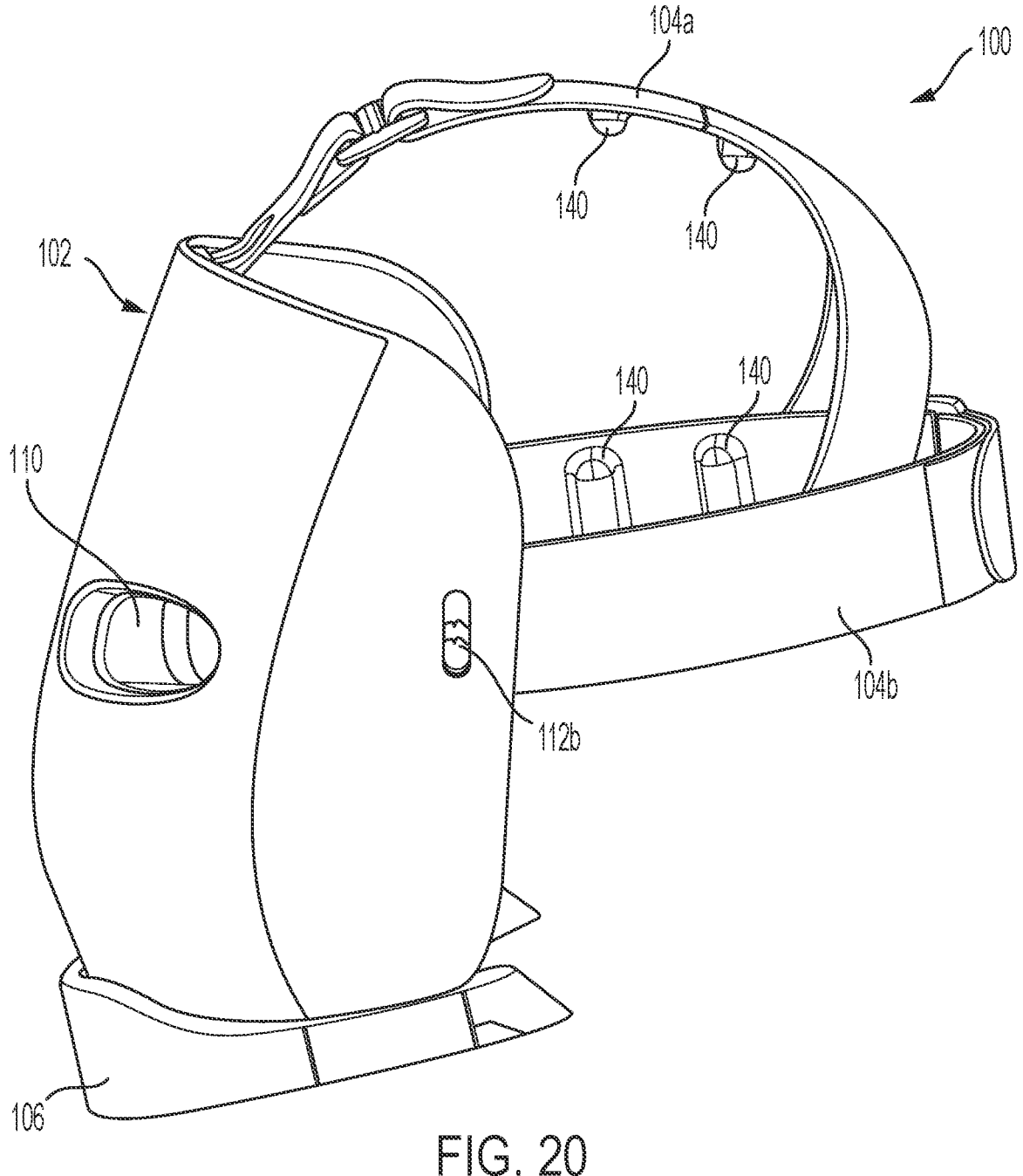
FIG. 20 illustrates a side view of the strap coupled to the mask assembly, according to embodiments of the present disclosure.
Figure 21A:
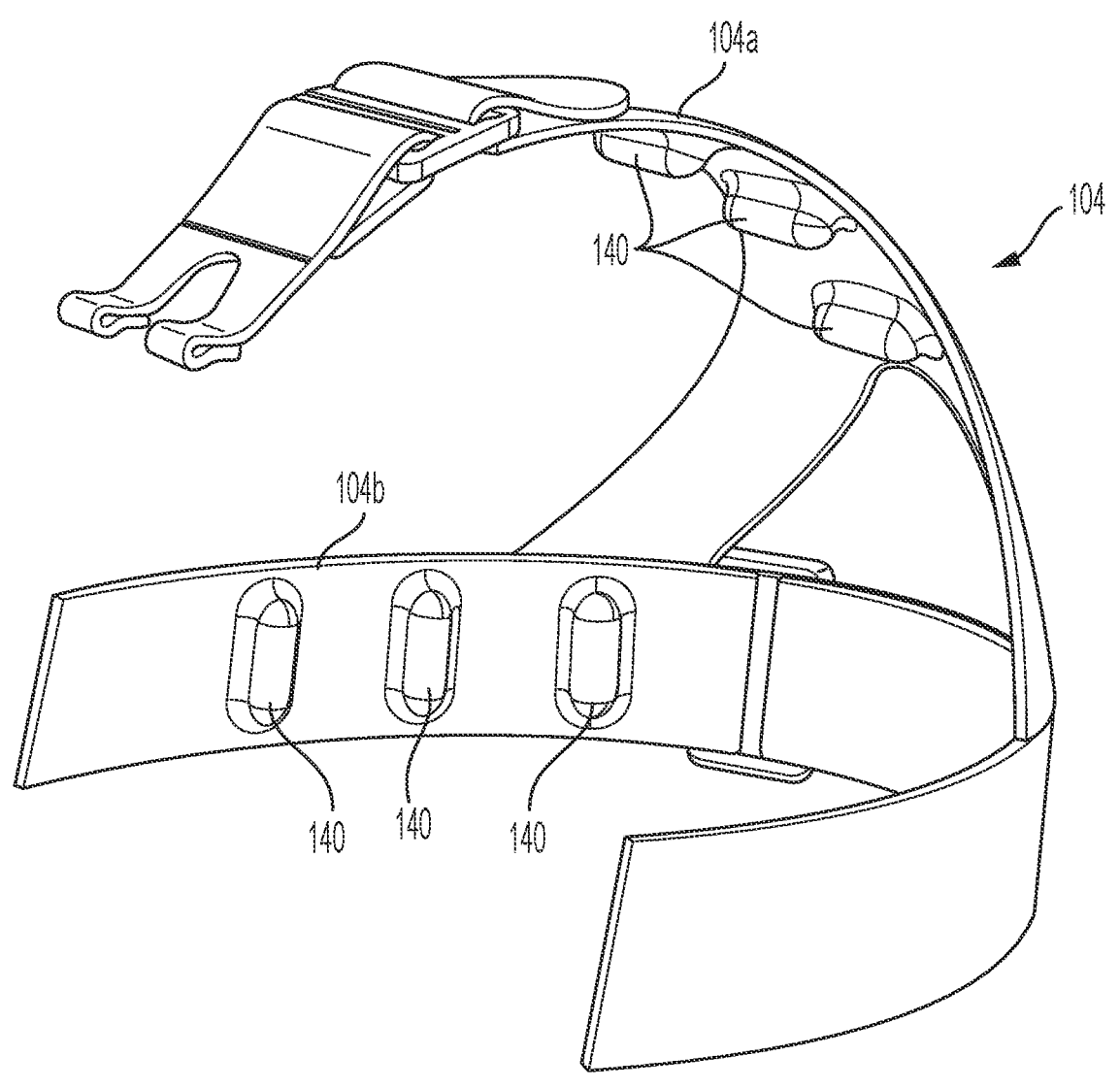
FIG. 21A illustrates a perspective view of a strap of the mask assembly, according to embodiments of the present disclosure.

FIG. 20 illustrates a side view of the strap 104 coupled to the mask assembly 100, according to embodiments of the present disclosure. FIG. 21A illustrates a perspective view of the strap 104 of the mask assembly 100, according to embodiments of the present disclosure. In some embodiments, the strap 104 may include a top portion 104a and a lateral portion 104b. The top portion 104a may be in contact with the top of a user's head, and the lateral portion 104b may extend laterally from the sides of the user's head. In some embodiments, the top portion 104a of the strap 104 may extend along a longitudinal plane or sagittal plane of the user's head. In some embodiments, the lateral portion 104b of the strap 104 may extend along a lateral plane or transverse plane of the user's head. In some embodiments, the lateral portion 104b of the strap 104 may be referred to herein as a bottom portion of the strap. In some embodiments, the strap 104 may include one or more bands and one or more buckles used to fasten or secure the one or more bands around the user's head. A plurality of vibration motors may be arranged in at least one of or both of the top portion 104a and lateral portion 104b of the strap 104. In some embodiments, the strap 104 may include one or more additional layers that are arranged over the vibration motors 140.

Figure 21B:
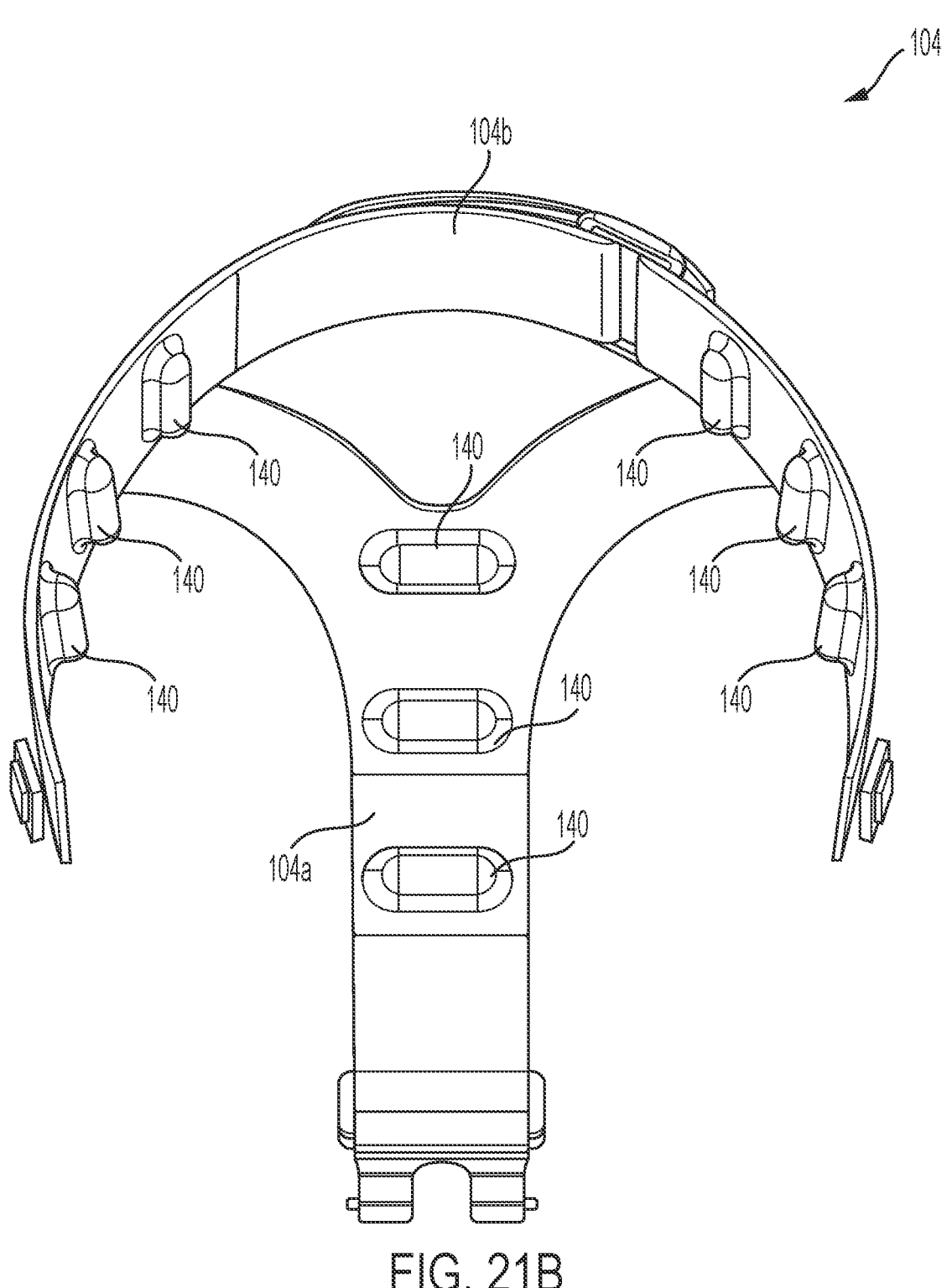
FIG. 21B illustrates a bottom view of the strap, according to embodiments of the present disclosure.

FIG. 21B illustrates a bottom view of the strap 104, according to embodiments of the present disclosure. The strap 104 may include one or more fasteners or components used to attach the ends of the lateral portion 104b and an end of the top portion 104a to the mask portion 102. In some embodiments, a first end of the lateral portion 104b may be coupled to a region on the left side of the mask portion 102, and a second end of the lateral portion 104b may be coupled to a region on the right side of the mask portion 102. In some embodiments, a first end of the top portion 104a may be coupled to a top region of the mask portion 102. In some embodiments, a second end of the top portion 104a may be coupled to a middle region of the lateral portion 104b of the strap 104. In some embodiments, the different ends of the strap portions (104a and 104b) may be attached to the respective locations by one or more of a locking, clipping, and/or magnetic mechanism, a buckle, a clasp, or the like.

Figure 21C:
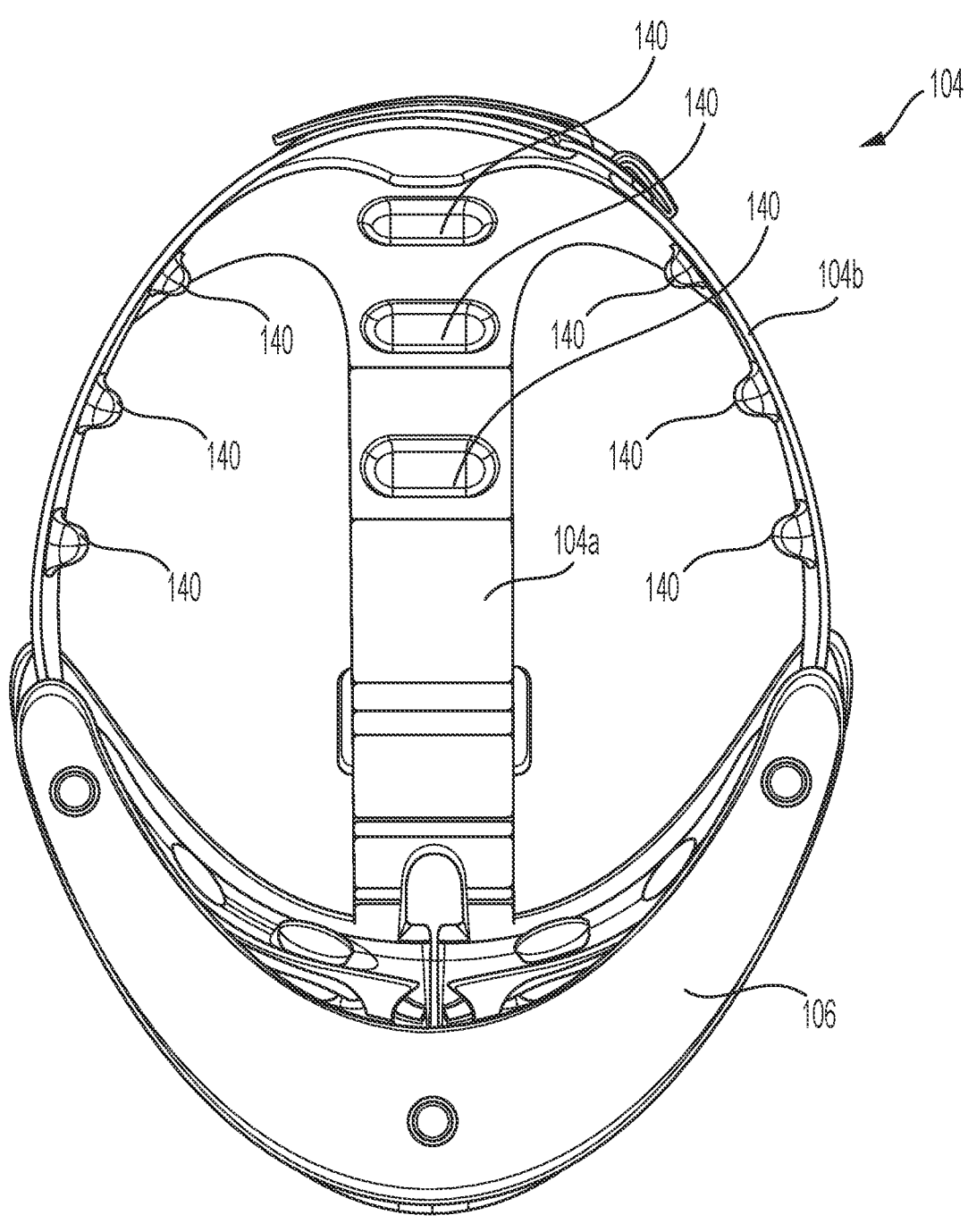
FIG. 21C illustrates a bottom view of the strap coupled to the mask assembly, according to embodiments of the present disclosure.
Figure 21D:
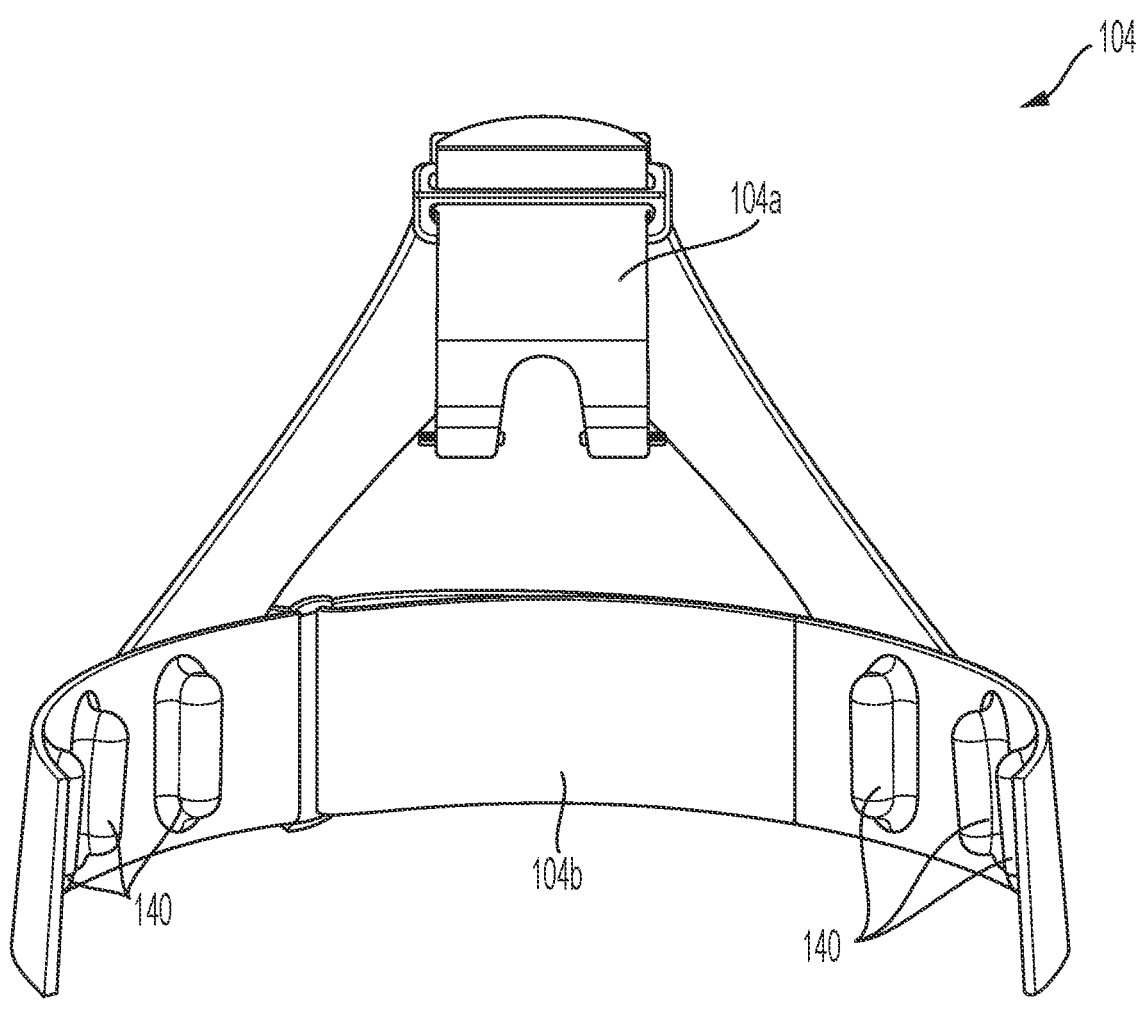
FIG. 21D illustrates a front view of the strap, according to embodiments of the present disclosure.

FIG. 21C illustrates a bottom view of the strap 104 coupled to the mask assembly 100 and stand 106, according to embodiments of the present disclosure. FIG. 21D illustrates a front view of the strap 104, according to embodiments of the present disclosure.

It is to be appreciated that the Detailed Description section, and not the Summary and Abstract sections, is intended to be used to interpret the claims. The Summary and Abstract sections may set forth one or more but not all exemplary embodiments of the present disclosure as contemplated by the inventor(s), and thus, are not intended to limit the present disclosure and the appended claims in any way.

Embodiments of the present disclosure have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

What is claimed is:

1. A mask apparatus comprising:
a mask portion comprising:
   an outer layer;
   one or more middle layers comprising a plurality of light emitting diodes (LEDs) and one or more printed circuit board (PCB) members; and
   an inner layer;
an eye portion coupled to and extending away from the inner layer of the mask portion, the eye portion comprising:
   a silicone layer configured to cover an area around a user's eyes;
   a first plurality of vibration motors encapsulated in the silicone layer; and
   structural components arranged adjacent to the silicone layer for housing the first plurality of vibration motors,
   wherein the silicone layer comprises a raised edge that allows only the eye portion and the first plurality of vibration motors to contact the area around the user's eyes;
one or more openings for the user's eyes, the one or more openings extending through the mask portion and the eye portion;
an eye cover configured to block light, from the plurality of LEDs, from the user's eyes when the user is wearing the mask, wherein the eye cover is arranged in a portion of the one or more openings; and
a strap coupled to the mask portion,
wherein the mask portion further comprises:
   a first panel and a second panel, each panel having, therein, the outer layer, the one or more middle layers, and the inner layer; and
   a hinge assembly extending along a longitudinal axis at the center of the mask portion from tops of the first and second panels to bottoms of the first and second panels, the first and second panels joined together by the hinge assembly, and wherein the one or more openings comprise a first opening and a second opening, the first opening arranged in the middle of the first panel, and the second opening arranged in the middle of the second panel, and wherein the eye portion is configured so that the mask portion is spaced apart from the user's face by a distance.

2. The mask apparatus of claim 1, wherein the hinge assembly is configured to allow outward and inward movement of the first and the second panels.

3. The mask apparatus of claim 1, wherein the inner layer of the mask portion comprises silicone and is configured to cover the user's face, and wherein the inner layer is configured to emit light from one or more LEDs of the plurality of LEDs towards the user's face.

4. The mask apparatus of claim 1, wherein the plurality of LEDs is configured to emit at least one of a red light, blue light, or infrared light.

5. The mask apparatus of claim 1, wherein the one or more PCB members are electrically connected to the plurality of LEDs and the first plurality of vibration motors, and wherein the plurality of LEDs and the first plurality of vibration motors are communicatively coupled to an electronic device configured to control one or more operations of the plurality of LEDs and the first plurality of vibration motors through the one or more PCB members.

6. The mask apparatus of claim 1, wherein the first plurality of vibration motors comprises a plurality of coin motors.

7. The mask apparatus of claim 1, wherein the strap comprises a second plurality of vibration motors, the second plurality of vibration motors comprising a plurality of pill-shaped motors.

8. The mask apparatus of claim 1, wherein the first plurality of vibration motors is arranged concentrically to the one or more openings for the user's eyes.

9. The mask apparatus of claim 1, further comprising:

a proximity sensor coupled to the inner layer of the mask portion and configured to determine a distance between the inner layer and the user's face.

10. The mask apparatus of claim 1, wherein the plurality of LEDs is configured to provide light therapy to treat a user's skin.

11. The mask apparatus of claim 1, wherein the first plurality of vibration motors is configured to provide vibration therapy for a user's skin.

12. The mask apparatus of claim 1, wherein the strap comprises a first strap portion configured to extend along a sagittal plane of the user's head, and wherein the strap further comprises a second strap portion configured to extend along a transverse plane of the user's head.

13. The mask apparatus of claim 12, wherein a first end of the first strap portion is coupled to a top region of the mask portion, and wherein a second end of the first strap portion is coupled to a middle region of the second strap portion.

14. The mask apparatus of claim 12, wherein a first end of the second strap portion is coupled to a left region of the mask portion, and wherein a second end of the second strap portion is coupled to a right region of the mask portion.

15. The mask apparatus of claim 1, wherein the plurality of LEDs are configured to emit a light having an emittance of 50 mW-60 mW and a peak wavelength of 820 nm-840 nm.

16. The mask apparatus of claim 1, further comprising a stand configured to be removably received in bottom portions of the first and second panels, respectively, in a fixed position.

17. The mask apparatus of claim 1, further comprising one or more buttons disposed on an outward-facing lateral side of the mask portion and configured to control functions of the mask apparatus.

18. The mask apparatus of claim 1, wherein a horizontal length of the mask portion is configured to allow at least one of the first panel or the second panel to move outwardly to accommodate a first head size and inwardly to accommodate a second head size, wherein the first head size and the second head size are different, and wherein the strap coupled to the mask portion is adjustable to different sizes to fit the first head size and the second head size.

19. The mask apparatus of claim 1, wherein the silicone layer is transparent such that the plurality of LEDs emit light through the silicone layer to treat the user's skin.

20. A method comprising:

obtaining a mask apparatus, wherein the mask apparatus comprises a mask portion, an eye portion coupled to and extending away from the mask portion, one or more openings for a user's eyes, an eye cover, and a strap coupled to the mask portion, wherein the mask portion comprises an outer layer, one or more middle layers comprising a plurality of light emitting diodes (LEDs) and one or more printed circuit board (PCB) members, and an inner layer, wherein the eye portion comprises a silicone layer configured to cover an area around the user's eyes, a plurality of vibration motors encapsulated in the silicone layer, and structural components arranged adjacent to the silicone layer for housing the plurality of vibration motors, wherein the silicone layer comprises a raised edge that allows only the eye portion and the first plurality of vibration motors to contact the area around the user's eyes, wherein the eye cover is arranged in a portion of the one or more openings and is configured to block light, from the plurality of LEDs, from the user's eyes when the user is wearing the mask, wherein the one or more openings extend through the mask portion and the eye portion, wherein the mask portion further comprises a first panel and a second panel, each panel having the outer layer, the one or more middle layers, the inner layer, and a hinge assembly extending along a longitudinal axis at the center of the mask portion from tops of the first and second panels to bottoms of the first and second panels, the first and second panels joined together by the hinge assembly, and wherein a horizontal length of the mask portion is configured to allow at least one of the first panel or the second panel to move outwardly to accommodate a first head size and inwardly to accommodate a second head size, wherein the first head size and the second head size are different, and wherein the one or more openings comprise a first opening and a second opening, the first opening arranged in the middle of the first panel, and the second opening arranged in the middle of the second panel;

positioning the mask apparatus over a user's face by adjusting the mask portion to accommodate one of the first head size or the second head size;

positioning the eye portion on and in-contact with the user's face such that the mask portion is spaced apart from the user's face by a treatment distance; and providing, to the user's face, at least one of vibration therapy through one or more vibration motors of the plurality of vibration motors or light therapy through one or more LEDs of the plurality of LEDs to the user's face.

21. The method of claim 20, further comprising the steps of:

detecting a mask distance between the mask portion and the user's face with a proximity sensor of the mask apparatus, and adjusting a power of the one or more LEDs based on the mask distance.

\* \* \* \* \*